US011253151B2

(12) United States Patent
Zhang

(10) Patent No.: US 11,253,151 B2
(45) Date of Patent: Feb. 22, 2022

(54) MULTISPECTRAL AND HYPERSPECTRAL OCULAR SURFACE EVALUATOR

(71) Applicant: Aizhong Zhang, Rochester, NY (US)

(72) Inventor: Aizhong Zhang, Rochester, NY (US)

( * ) Notice: Subject to any disclaimer, the term of this patent is extended or adjusted under 35 U.S.C. 154(b) by 316 days.

(21) Appl. No.: 16/563,913

(22) Filed: Sep. 8, 2019

(65) Prior Publication Data

US 2021/0068655 A1 Mar. 11, 2021

(51) Int. Cl.
| | |
|---|---|
| *A61B 3/15* | (2006.01) |
| *A61B 3/00* | (2006.01) |
| *A61B 3/10* | (2006.01) |
| *A61B 3/103* | (2006.01) |
| *A61B 3/14* | (2006.01) |

(52) U.S. Cl.
CPC ............ *A61B 3/152* (2013.01); *A61B 3/0008* (2013.01); *A61B 3/101* (2013.01); *A61B 3/103* (2013.01); *A61B 3/145* (2013.01)

(58) Field of Classification Search
CPC ....... A61B 3/152; A61B 3/0008; A61B 3/101; A61B 3/103; A61B 3/145; A61B 3/107
USPC ......................................................... 351/206
See application file for complete search history.

(56) References Cited

U.S. PATENT DOCUMENTS

| | | |
|---|---|---|
| 324,162 A | 8/1885 | Porter |
| 5,500,697 A | 3/1996 | Fujieda |
| 5,684,562 A | 11/1997 | Fujieda |
| 5,841,511 A | 11/1998 | D'Souza et al. |
| 5,864,383 A | 1/1999 | Turner et al. |
| 6,045,503 A | 4/2000 | Grabner et al. |
| 6,601,956 B1 | 8/2003 | Jean et al. |
| 6,654,553 B2 | 11/2003 | Shibata et al. |
| 6,692,126 B1 | 2/2004 | Xie et al. |
| 6,937,885 B1 | 8/2005 | Lewis et al. |
| 6,992,775 B2 | 1/2006 | Soliz et al. |
| 7,121,666 B2 | 10/2006 | Tseng et al. |
| 7,336,360 B2 | 2/2008 | Oka et al. |

(Continued)

OTHER PUBLICATIONS

Vyas, Banerjee, and Burlina. "Estimating physiological skin parameters from hyperspectral signatures." Journal of biomedical optics 18, No. 5 (2013): 057008.

(Continued)

*Primary Examiner* — Mohammed A Hasan
(74) *Attorney, Agent, or Firm* — Lynne M. Blank, Esq.

(57) ABSTRACT

A multispectral or hyperspectral ocular surface evaluating device is disclosed, comprising an illumination projector, which comprises a broadband illumination source panel and a polarizing structure to illuminate an ocular surface and adjacent structures of an eye and project a pattern on the ocular surface; an imaging system to form images; a detection system to record the images with a plurality of spectral channels in visible and near infrared spectra; and a computer to display and analyze the images. Also disclosed is a method of evaluating ocular surface health using a multispectral or hyperspectral ocular surface evaluating device, which comprises illuminating an ocular surface and adjacent structures of an eye with polarized light from an illumination projector; forming images with the imaging system; recording images formed on the detection system; digitally processing the recorded images; and analyzing the recorded images to evaluate ocular surface health with the computer.

20 Claims, 22 Drawing Sheets

(56) References Cited

U.S. PATENT DOCUMENTS

| | | | |
|---|---|---|---|
| 7,611,245 | B2 | 11/2009 | Carbonari |
| 7,623,236 | B2 | 11/2009 | Oka et al. |
| 7,866,819 | B2 | 1/2011 | Tuan |
| 8,224,425 | B2 | 7/2012 | Freeman et al. |
| 8,249,695 | B2 | 8/2012 | Grenon et al. |
| 8,368,889 | B2 | 2/2013 | Schwiegerling et al. |
| 8,591,033 | B2 | 11/2013 | Korb et al. |
| 8,600,484 | B2 | 12/2013 | Grenon et al. |
| 8,649,008 | B2 | 2/2014 | Kashani et al. |
| 8,654,328 | B2 | 2/2014 | Tkaczyk et al. |
| 8,820,935 | B2 | 9/2014 | Steinmueller |
| 8,899,753 | B2 | 12/2014 | Steinmueller |
| 9,002,085 | B1 | 4/2015 | Solanki et al. |
| 9,198,578 | B2 | 12/2015 | Zuzak et al. |
| 9,204,805 | B2 | 12/2015 | Panasyuk et al. |
| 9,320,439 | B2 | 4/2016 | Arita et al. |
| 9,642,520 | B2 | 5/2017 | Korb et al. |
| 9,693,682 | B2 | 7/2017 | Korb et al. |
| 9,907,471 | B2 | 3/2018 | Caves et al. |
| 9,968,285 | B2 | 5/2018 | Valsan et al. |
| 10,893,796 | B2 * | 1/2021 | Wang .................. A61B 3/1005 |
| 2011/0273550 | A1 | 11/2011 | Amano et al. |
| 2019/0183332 | A1 | 6/2019 | Zhang |
| 2019/0254515 | A1 | 8/2019 | Zhang |

OTHER PUBLICATIONS

Smola, Alex J., and Bernhard Schölkopf. "A tutorial on support vector regression." Statistics and computing 14, No. 3 (2004): 199-222.

Mejia-Barbosa, Yobani, and Daniel Malacara-Hernández. "A review of methods for measuring corneal topography." Optometry and vision science 78, No. 4 (2001): 240-253.

Sweeney, Deborah F., Thomas J. Millar, and Shiwani R. Raju. "Tear film stability: a review." Experimental Eye Research 117 (2013): 28-38.

Mainstone, Julia C., Adrian S. Bruce, and Timothy R. Golding. "Tear meniscus measurement in the diagnosis of dry eye." Current eye research 15, No. 6 (1996): 653-661.

Downie, Laura E., Peter R. Keller, and Algis J. Vingrys. "Assessing ocular bulbar redness: a comparison of methods." Ophthalmic and Physio. Optics 36, No. 2 (2016):132-139.

Pult, Heiko, and Jason J. Nichols. "A review of meibography." Optometry and Vision Science 89, No. 5 (2012): E760-E769.

A Reiko, K Itoh, K Inoue, S Amano "Noncontact infrared meibography to document age-related changes of the meibomian glands in a normal population" Ophth 115, No. 5 (2008)911-915.

Zhang, Salahura, Kottaiyan, Yoon, Aquavella, Zavislan. "Multimodal imaging of ocular surface of dry eye subjects" Multimodal Biomed Imag XI, vol. 9701, p. 97010H (2016).

Goto, Dogru, Kojima, and Tsubota "Computer-synthesis of an interference color chart of human tear lipid layer, by a colorimetric approach" InvestOphth&VisSci 44, No. 11 (2003).

Zhang, Maki, Salahura, Kottaiyan, Yoon, Hindman, Aquavella, Zavislan "Thermal anal of dry eye subjects & the thermal impulse pert model of ocular surface" ExpEyeRsch 132(2015).

Abreau, Callan, Kottaiyan, Zhang, Yoon, Aquavella, Zavislan, Hindman "Temps of the Ocular Surface, Lid, and Periorbital Regions of Sjögren's, Evaporative, and Aqueous-Def . . . ."

Oka, Saito "Snapshot complete imaging polarimeter using Savart plates" In Infrared Detectors and Focal Plane Arrays. VIII, vol. 6295, p. 629508. Int.Soc for Optics and Ph ('06).

DeHoog, Edward, Haitao Luo, Kazuhiko Oka, Eustace Dereniak, and James Schwiegerling. "Snapshot polarimeter fundus camera." Applied optics 48, No. 9 (2009): 1663-1667.

Oka, Kazuhiko, and Takayuki Kato. "Spectroscopic polarimetry with a channeled spectrum." Optics Letters 24, No. 21 (1999): 1475-1477.

Sabatke, Locke, Dereniak, Descour, Garcia, Hamilton, and McMillan. "Snapshot imaging spectropolarimeter." Optical engineering 41 (2002).

Oka, Haga, Michida "Snapshot Mueller-matrix spectropolarimeter using spectral and spatial carriers" In Polarization Science and Remote Sensing VII, vol. 9613, p. 96130E (2015).

Hagen, Gao, Tkaczyk, Kester "Snapshot advantage: a review of the light collection improvement for parallel high-dimensional measurement systems" Opt Eng 51, No. 11 (2012).

Westphal, Kaltenbach, Wicker "Corneal birefringence measured by spectrally resolved Mueller matrix ellipsometry and implications for non-invasive glucose monitoring" (2016).

Zhou, and Weinreb "Individualized compensation of anterior segment birefringence during scanning laser polarimetry" Inv. ophth. & vis sci 43, No. 7 (2002): 2221-2228.

Bueno, Juan M., and Pablo Artal. "Double-pass imaging polarimetry in the human eye." Optics letters 24, No. 1 (1999): 64-66.

Twietmeyer, Chipman, Elsner, Zhao, VanNasdale "Mueller matrix retinal imager with optimized polarization conditions" Optics express 16, No. 26 (2008): 21339-21354.

* cited by examiner

70 Tear film lipid layer

71 Tear film aqueous layer

72 Tear film mucous layer

73 Corneal epithelium

74 Bowman's layer

75 Corneal stroma

76 Descemet's membrane

77 Corneal endothelium

78 Aqueous humor

| 79 Iris | | 79 Iris |

80 Lens

FIG. 16

96 Conjunctiva

97 Tenon's capsule

98 Episclera

99 Scleral stroma

109 Lamina fusca

FIG. 18

MULTISPECTRAL AND HYPERSPECTRAL OCULAR SURFACE EVALUATOR

FIELD OF THE INVENTION

This invention relates to the field of ophthalmology. In particular, this invention relates to the evaluation of the ocular surface health with multispectral and hyperspectral imaging.

BACKGROUND OF THE INVENTION

The ocular surface is the anterior interface between an eye and the ambient environment. It is composed of the tear film, cornea, limbus, and conjunctiva. Adnexal structures of the ocular surface, such as the lacrimal gland, the lacrimal drainage apparatus, the eyelids, and the eyelashes, are essential for proper function of the ocular surface.

Tear film is a thin, protective film that covers the exposed areas of an ocular surface with eyelid margins as its boundaries. It's essential to the visual acuity and the immune defense functions of the ocular surface. Chronic deficiencies in tear film will result in dry eye syndrome. Patients with dry eye syndrome either cannot secrete enough tears or their tear quality is not good enough. Quantitative measurements of the tear film are crucial to dry eye diagnosis.

Tear film is composed of three layers anterior to the corneal epithelial cells, including the mucous layer, the aqueous layer and the lipid layer. The tear film thickness is reported to be around 3 µm. The posterior mucous layer contains mucins secreted by the goblets cells in the conjunctiva. The mucous layer forms a viscoelastic matrix to stabilize the tear film on the corneal epithelium. The middle aqueous layer is the major watery part of the tear film, which contains a number of nutrients and proteins, such as globulins, lysozyme, lactoferrin, etc. The aqueous layer is secreted from the lacrimal gland, and it is essential for spreading of the tear film and regulating tear osmolarity. The lipid layer is the most anterior part of the tear film, and its thickness is usually in the order of 1 to 100 nm. It is secreted by the meibomian glands, which are tens of vertical glands lined up inside the tarsal plates of both upper and lower eyelids. The lipid layer serves to prevent and reduce evaporation, and enhance the tear film stability.

Various diagnostic methods have been developed to evaluate the ocular surface. The keratoscope was invented by the Portuguese physician Antonio Placido in 1880, which measures the reflected image off the human cornea of a disk with a central hole, bearing concentric black and white ring patterns. The disk has been referred to as Placido's disk. A large number of variations and improvements of the keratoscope and the corresponding topography reconstruction algorithms have been developed ever since, mainly due to the increasing significance and demand of precise corneal topography measurements for contact lens fitting and keratorefractive surgeries. Projectors with various shapes, colors and ring or mire patterns to replace the original Placido's disk have been described in the prior art, and the basic principle of using the reflected images off the cornea to retrieve the corneal topography remains the same.

Every time after a blink, the tear film is replenished and redistributed, and as the eye remains open for a period of time, the tear film gradually gets thinner, and eventually breaks up at some spots, due to surface tension or evaporation. Clinically, the time interval between the last blink and the first random appearance of a tear break up spot or a dry spot in the tear film is referred to as the tear breakup time (TBUT), and it's indicative of the tear film stability. Conventionally, a TBUT measurement requires the staining of the ocular surface with fluorescein, since the dry spot will be clearly visible under a slit-lamp after the staining. However, it has been reported that the instillation of fluorescein affects the tear stability. Several non-invasive measurement methods of TBUT without staining have been known in the prior art to obtain TBUT more objectively, which measure the change in the reflected images off the cornea of a grid or ring pattern.

Tear meniscus height (TMH) measurement is an indirect method to evaluate the tear volume widely used in clinics. A tear meniscus is formed between the eyelid inner surface and the globe of the eye, and along the superior and interior eye lid margins. It is estimated that the tear menisci hold 75% to 90% of the total tear volume. The larger the tear meniscus height is, the larger the tear volume is. Because of the frequent movement of the upper eyelid, and the obscuration by the eyelashes, usually only the lower tear meniscus is measured clinically. A tear meniscus height of ≤0.2 mm is sometimes chosen to be indicative of dry eye. A number of techniques have been developed to measure TMH. TMH can be measured with or without fluorescein to enhance the contrast, in frontal view or in a cross-sectional view, depending on the technique employed. The simplest TMH measurement is done with a slit lamp, where a reticule is included as part of the eyepiece system. If fluorescein is used, a color filter is usually employed to enhance the contrast. Besides slit lamps, several other instruments such as optical coherence tomography (OCT) systems or optical pachymeters can also be used for TMH evaluation. In an OCT system, TMH is obtained in a cross-sectional image of the anterior part of the eye.

Bulbar hyperemia is often referred to as bulbar redness due to the redness appearance of the eye caused by the vasodilation of the conjunctival blood vessels. Bulbar redness is a common symptom of a number of ophthalmic diseases such as dry eye syndrome, glaucoma, scleritis, keratitis, xerophthalmia and so on. Clinically, bulbar redness is either graded by comparing with reference to standardized descriptions or illustrations by clinicians subjectively, or the images of the eye are analyzed digitally and objectively along an arc, a line or within a selected region of interest (ROI) of the conjunctival image.

Meibography uses the different absorption, translucency, reflection and scattering of light by the meibomian glands, compared to adjacent skin tissues, to form an image with high enough contrast to distinguish the meibomian glands morphology and distribution within the upper and lower eyelids. Traditionally, there are two types of meibography, one with transillumination, and the other with direct illumination. Meibography was invented by Tapie in 1977 based on clinical tests. Later, infrared light was used to enhance the contrast. The early meibographers usually employed transillumination. In 2008, Arita et al. reported a non-contact meibography system that uses direct illumination to collect reflective images. Later, more direct-illumination, non-contact meibographers have been developed, partly because the direct-illumination type is more comfortable for the patients during measurements, compared with the earlier transillumination type.

Biomicroscopy of the inner lid margin has been used to directly inspect individual meibomian gland orifices at the inner side of the eyelids close to the base of eyelashes. With this method, potential obstruction of the meibomian gland orifices by solidified lipids, a condition that might lead to meibomian gland dysfunction, is directly visible to the examiner.

The lipid layer thickness of the tear film can be evaluated based on the reflected pattern of color due to the interference of multiple-reflection at the thin lipid layer. Similar phenomena in daily life include the iridescent colors of a soap bubble, and the colors of a thin oil film on a wet ground. The analysis of the reflected color in the red, green and blue color channels in the visible spectrum could quantitatively determine the thickness of the lipid layer.

With polarized light illumination onto the ocular surface, the detected signal will contain the reflected light from the iris, which is partially polarized. The iris background light will degrade the accuracy of the lipid layer thickness retrieval. To minimize the effect of iris back scattering, precise characterization of the corneal birefringence is desired. Further, corneal birefringence also indicates the biomechanical structure of the cornea, especially useful for inspection after a refractive surgery, such as LASIK or PRK. Corneal birefringence is mostly due to the corneal stroma, which forms the bulk of the cornea. The corneal stroma comprises about 300 to 500 lamellae, increasing from the center to corneal periphery. Each lamella is made of collagen fibril bundles (mostly of type I collagen) and is inherently birefringent. The stacking and interweaving of these birefringent lamellar layers lead to not only a linear retardance, but an optical rotation as well, which is more complicated than a simple uniaxial or biaxial model. Generally speaking, corneal birefringence is relatively uniform in the central portion and its spatial retardance variation gradually increases towards the periphery. It is well known that there is a large interindividual variability of corneal birefringence. Even for the same eye, corneal birefringence is significantly dependent on the location and the incident angle.

Retinal polarimeter has been used to characterize corneal birefringence. The Henle's fiber layer of the fovea has a radial nerve fiber distribution, which could be used as a natural internal polarimeter of the human eye to measure the corneal birefringence. Either a "bowtie" method or a "screen" method could be used to retrieve the corneal birefringence, as described by Twietmeyer et al. in "Mueller matrix retinal imager with optimized polarization conditions." *Optics express* 16, no. 26 (2008). With the corneal birefringence quantified, the retinal nerve fiber layer thickness of the optic nerve head could be evaluated to identify and monitor the progression of glaucoma.

Thermal imaging has been reported to be used to distinguish different types of dry eye syndrome. With the calibration of the thermal emissivity of the eye and the analysis of the temperature cooling pattern after a blink, the thermal dynamical features, including the initial temperature, the steady state temperature and the thermal decay rate could be helpful in dry eye diagnosis.

The ocular surface evaluating device disclosed in this invention is a multispectral or hyperspectral device. Multispectral and hyperspectral imaging systems combine imaging with spectroscopy, hence both spatial and spectral properties of the object could be investigated. Usually, the total number of spectral bands in a multispectral imaging system is fewer than 20, and these spectral bands are formed by spectral filters or different detectors, etc. In contrast, a hyperspectral imaging system usually has hundreds or thousands of spectral channels, and a diffractive grating or other dispersive optical elements are employed. Although there is not a clear distinction on the number of spectral bands to clearly distinguish hyperspectral imaging from multispectral imaging, hyperspectral imaging generally captures a continual spectrum, with more spectral bands and higher spectral resolution, compared to multispectral imaging. Each resultant hyperspectral image is a three-dimensional data cube, known as a "hypercube", with two spatial dimensions (x, y), and one spectral dimension $\lambda$.

A conventional hyperspectral imaging system either records a two dimension area (x, y), and sequentially steps through the wavelength $\lambda$ dimension, or records a one dimensional slice of an object and disperses this slice along wavelength into a two dimension space of (x, $\lambda$), and scans along the orthogonal spatial dimension y. Further, hyperspectral Fourier transform imaging spectrometer could also record the 3D hypercube with similar optical throughput.

Recently, snapshot imaging spectrometers with higher optical throughput have been developed, which could record the 3D hypercube in a single snapshot. Various designs of these snapshot imaging spectrometers include computed tomographic imaging spectrometry (CTIS), coded aperture snapshot spectral imaging (CASSI), image mapping spectrometry (IMS), etc. have been described by Hagen, et al. in "Snapshot advantage: a review of the light collection improvement for parallel high-dimensional measurement systems." *Optical Engineering* 51, no. 11 (2012).

Multispectral and hyperspectral imaging techniques have been used in the prior art in medical imaging to inspect and diagnose diabetes, tumor, heart tissue ablation, fundus health and retinal diseases, etc., as described in U.S. Pat. Nos. 6,937,885, 6,992,775, 8,224,425, 8,649,008, 8,654,328, 9,002,085, 9,198,578, 9,204,805, 9,907,471, 9,968,285, etc.

Snapshot imaging polarimeter using Savart plates to add spatial carriers was developed by Oka and Saito as described in "Snapshot complete imaging polarimeter using Savart plates," *Infrared Detectors and Focal Plane Arrays VIII*, Vol. 6295. International Society for Optics and Photonics, 2006. Later, this technology was used to develop a snapshot fundus camera to analyze the retina as described in "Snapshot polarimeter fundus camera." *Applied optics* 48, no. 9 (2009).

Oka and Kato developed spectroscopic polarimetry with a channeled spectrum using high order retarders to add spectral carriers as described in "Spectroscopic polarimetry with a channeled spectrum." *Optics Letters* 24, no. 21 (1999). This technology was integrated with the computed tomography imaging spectrometer (CTIS) to form a snapshot imaging spectropolarimeter as described in "Snapshot imaging spectropolarimeter." *Optical engineering* 41 (2002).

Further, Oka et al. developed a snapshot Mueller-matrix spectropolarimeter using both spectral and spatial carriers, where high order retarders are used in the polarization state generator and Savart plates are used in the polarization state analyzer as described in "Snapshot Mueller-matrix spectropolarimeter using spectral and spatial carriers." *Polarization Science and Remote Sensing VII*, Vol. 9613. International Society for Optics and Photonics, 2015.

Even though the aforementioned techniques have been developed independently, there is a need for a novel instrument to adapt the available technologies for ocular surface examination, and integrate multiple key ocular surface measurements into one compact device. More importantly, there is a need to bridge a significant gap between multispectral and hyperspectral imaging and ocular surface evaluation. Further, polarimetry could add another dimension to ocular surface evaluation.

U.S. Pat. Nos. 8,820,935 and 8,899,753 describe a device that integrates some of these aforementioned ocular surface measurements, where a first monochromatic infrared light source and a further polychromatic visible light source are used. However, neither a hyperspectral detection system, nor polarization light control is employed, which will limit the information that can be extracted from the imaging systems.

Furthermore, in the prior art, the illumination for lipid layer thickness retrieval is limited to visible spectral channels, and the reflected color at each pixel is evaluated by comparing the red, green and blue three color channels with theoretical models, such as U.S. Pat. Nos. 7,121,666, 8,591,033, 9,642,520, 9,693,682, etc. Multispectral and hyperspectral imaging with more spectral channels in both visible and infrared spectra could provide much more detailed spectral reflectance information to increase the accuracy of lipid thickness measurement. Further, most of these tear film measurement instruments in the prior art are unable to properly distinguish tear film reflected light from the background noise of the iris scattered light.

Moreover, meibography was often done with infrared imaging, such as described in U.S. Pat. Nos. 8,249,695, 8,600,484, 9,320,439, and U.S. Pat. Application 20110273550, and the final resultant image of the meibomian glands are black and white grayscale images. The limited infrared spectrum potentially loses some critical pathological information.

U.S. patent application Ser. No. 16/278,087 by the same inventor as the current invention disclosed a multifunctional ophthalmic instrument, which integrates some of the functionalities of this invention, however, neither polarimetry, nor hyperspectral imaging is used.

This invention modifies some of these critical enabling technologies, and integrates polarimetric multispectral and hyperspectral imaging for ocular surface measurements.

SUMMARY OF THE INVENTION

It is an object of this invention to apply multispectral and hyperspectral imaging to an ocular surface to investigate both spatial and spectral ocular properties.

It is another object of this invention to add polarization control to an ocular surface evaluating device.

It is another object of this invention to apply spectropolarimetry to the field of ophthalmology.

It is yet another object to introduce a single device to image both the ocular surface and the retina, so that a retinal polarimeter is integrated to measure the corneal birefringence.

It is still another object to integrate multiple key ocular surface measurements into one compact device capable of a comprehensive analysis of the ocular surface.

The present invention relates to a multispectral or hyperspectral ocular surface evaluating device, the device comprising: an illumination projector with an aperture in a posterior end of the projector, wherein the illumination projector comprises a broadband illumination source panel and a polarizing structure to illuminate an ocular surface and adjacent structures of an eye and project a pattern on the ocular surface, wherein the broadband illumination source panel covers visible and near infrared spectra; an imaging system to form images of the ocular surface and adjacent structures; a detection system to record the images with a plurality of spectral channels in visible and near infrared spectra using spectral filters or dispersive optical elements; and a computer to display and analyze the images.

The invention also includes a method of evaluating ocular surface health using a multispectral or hyperspectral ocular surface evaluating device, comprising: illuminating an ocular surface and adjacent structures of an eye with polarized light from an illumination projector, covering visible and near infrared spectra; forming images of the ocular surface and adjacent structures of the eye with the imaging system; recording images formed on the detection system; digitally processing the recorded images to obtain spatial and spectral information; and analyzing the recorded images to evaluate ocular surface health with the computer.

BRIEF DESCRIPTION OF THE DRAWINGS

FIG. 16 presents one multilayer model of an ocular surface including cornea and tear film.

FIG. 18 presents one multilayer model of a sclera.

DETAILED DESCRIPTION OF THE INVENTION

Figure 1:
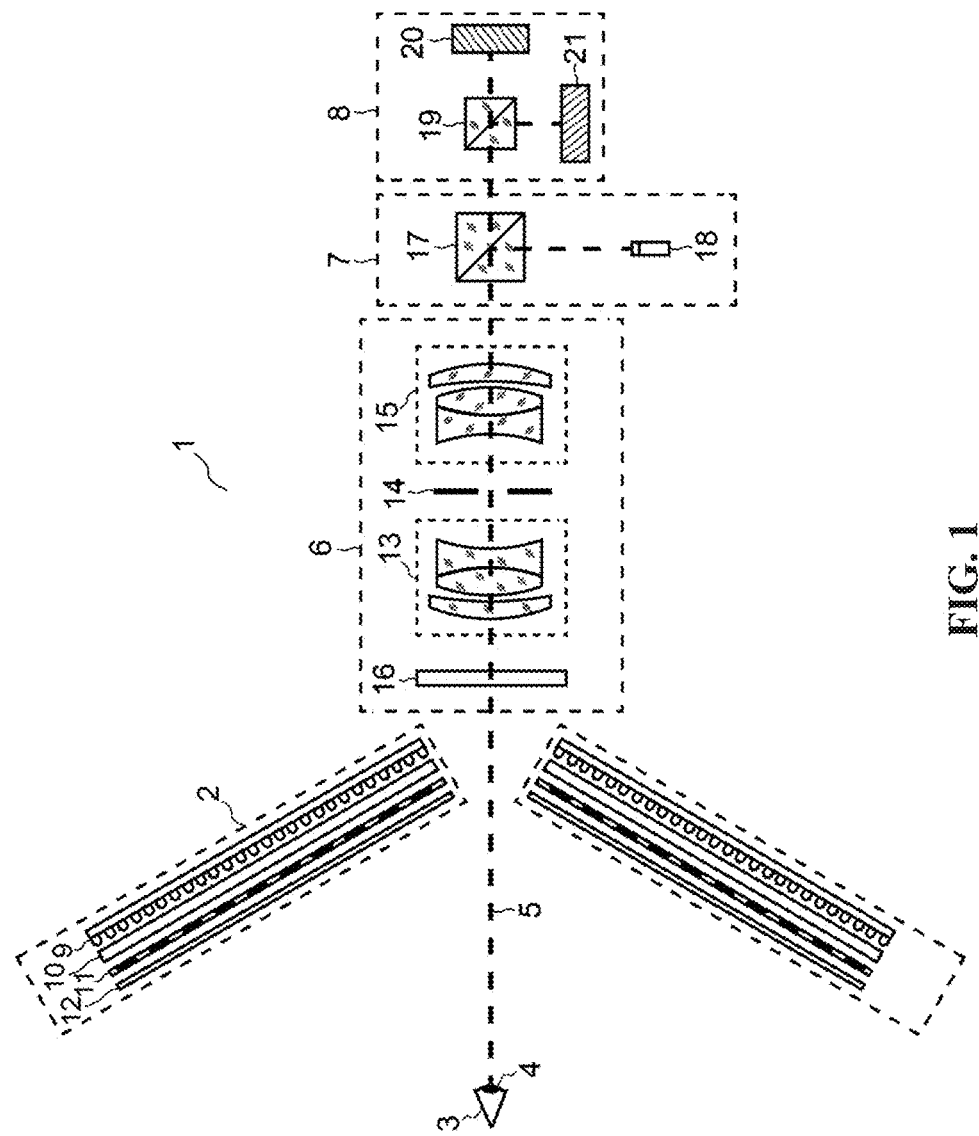
FIG. 1 presents one embodiment of a multispectral ocular surface evaluator.

FIG. 1 presents one embodiment of a multispectral ocular surface evaluator 1. An illumination system 2 directs light to an eye 3 and adjacent structures of a subject under measurement. The illumination system 2 comprises an illumination projector and associated mechanical and electronic accessories. The illumination projector comprises a broadband illumination source panel covering the visible and infrared spectra. Preferably, an adjustable chin rest (not shown) is used to support the subject at a comfortable position and maintain stability. In one preferred embodiment shown in FIG. 1, the illumination projector comprises a broadband illumination source panel 9 with visible and near infrared light-emitting diodes (LEDs), a diffusing structure 10 with one or more layers of translucent materials to distribute the light more uniformly, a projection pattern panel 11, and a polarizing structure 12. The polarizing structure 12 is used to control the polarization state distribution of incident light on the ocular surface and adjacent structures. 12 could simply be a linear, circular, or elliptical polarizer, or a sectional polarizing structure where different sections have different polarizing properties. 12 could also be a variable polarizer. Light is reflected off an ocular surface 4 of the eye 3, and part of the reflected light is collected into an imaging system 6 with an optical axis 5. The imaging system 6 could have many different embodiments, in one preferred embodiment as shown in FIG. 1, the imaging system 6 comprises a double Gauss lens group, with a first Gauss lens group 13, an aperture stop 14, and a second Gauss lens group 15. In some embodiments, the imaging system 6 also comprises a polarization analyzing structure 16. The polarization analyzing structure 16 could be placed in front of all the lens groups (as shown in FIG. 1), inside the lens groups or behind the lens groups. Preferably, the polarization analyzing structure 16 could be removed out of the optical path for some functionalities, such as corneal topography measurements, to avoid the complicating effect of the iris back scattered light coupled with corneal birefringence. An eye alignment system 7 could be used to align the eye with the optical axis 5 of the imaging system. The eye alignment system 7 could be placed either in front of, or after the imaging system 6. Although, in many cases, the preferred non-vignetting size of 7 tends to be smaller, if 7 is placed behind the imaging system 6 and before the detection system 8, as shown in FIG. 1, which could lead to a more compact system. The eye alignment system 7 comprises a light source 18, which is aligned coaxially with the imaging system, via a beamsplitter 17. After passing the imaging system 6 and the eye alignment system 7, light reaches a detection system 8. In FIG. 1, the detection system 8 is a multispectral detection system, which comprises a beamsplitter 19 to split light into a visible branch and an infrared branch. A visible detector 20 and an infrared detector 21 are used to match the two branches. The visible detector 20 could be a visible detector with red (R), green (G) and blue (B) three color channels, and the infrared detector 21 could be a monochromatic infrared detector. The detection system 8 could have more dichroic beamsplitters or detector filters and matching detectors to have more spectral channels. The embodiment of a detector could be a charge-coupled device (CCD), a complementary metal-oxide-semiconductor (CMOS), or other functionally similar recording devices.

The illumination system 2 is a broadband illumination system covering the visible and infrared spectra. In one embodiment, the broadband illumination source panel 9 comprises white LEDs and near-infrared LEDs. Preferably, the visible set of LEDs and the infrared set of LEDs are separately controlled, and each set is arranged to generate a relatively uniform light illumination. The projection pattern panel 11 has a structured pattern, which could be a pattern of black and white concentric rings (Placido's rings) with appropriately chosen width of each ring, colorful concentric rings, concentric rings and orthogonal radial lines, etc. The illumination projector has an aperture in the posterior end to allow light to pass through and enter the imaging system. Preferably, the geometric shape of the illumination projector is rotationally symmetric, such as a conical frustum, a spherical bowl, an ellipsoidal bowl, or a cylindrical shape with one end facing the eye, and the other end facing the imaging system.

Further, the illumination system 2 could project dynamic patterns. In one embodiment of a dynamic illumination projector, it comprises a curved organic light-emitting diode (OLED) display to generate dynamic patterns and a polarizer to polarize the illumination light. The OLEDs in the display includes both visible OLEDs and infrared OLEDs, such that the illumination light output in both visible and infrared are relatively uniformly distributed. The OLED display presents dynamically evolving projection patterns, which could improve corneal topography measurement accuracy by moving the edges of the ring or grid patterns to minimize data interpolation during topography retrieval.

To optimize the measurement accuracy, preferably, the subject is requested to fixate upon a light source 18 in the eye alignment system 7. The light source 18 could be a single light-emitting diode (LED), an LED with a collimating lens group, a properly positioned optical fiber with a collimating lens group, a low-power or attenuated laser source in the visible spectrum with the output power density much below maximum permissible exposure (MPE) for a human eye, or a combination of a lens and a microdisplay, etc. The preferred splitting ratio of the beamsplitter 17 is such that the majority of the light reflected from the object, ~90% for example, enters into the detection system, and only a small fraction of the light, ~10% for example, goes to the branch for eye fixation and alignment.

Note that for any subject with a normal retina, the eye alignment system 7 could help with fixation. However, for patients with some retinal diseases, such as diabetic retinopathy, central scotoma, peripheral neuropathology, etc., the patients may have difficulty in fixating. In that case, the reflected images off the ocular surface of the projection pattern panel 11 could be used to register the image series to minimize the effects of involuntary eye movements.

Sometimes, the adjacent structures of the ocular surface, instead of the ocular surface itself are of interest, such as the case in meibography, hence eye fixation might not be appropriate any more. During these measurements, the recorded images are displayed in the computer in real time to adjust the relative position of the subject to optimize the image quality.

The embodiments of the polarization analyzing structure 16 could be an analyzer made of a linear polarizer, a circular analyzer, an elliptical analyzer. 16 could also be a rotating polarizer, or a variable analyzer based on liquid crystals or other adjustable birefringent materials. The simplest embodiment of 16 is a fixed analyzer, and the transmitted polarization state of 16 is chosen such that the reflected light off the cornea surface is mostly transmitted into the rest of the optical system. For example, if the illumination light from 2 is left hand circularly polarized light, after corneal reflection, it will turn into mostly right hand circularly polarized light, hence 16 should be a circular analyzer to allow surface reflected right hand circularly polarized light to pass through.

However, such a fixed analyzer of 16 won't be able to properly distinguish tear film reflected light from the background noise of the iris scattered light. The iris scattered background light also impairs most of the tear film analyzing instruments in the prior art. In a preferred embodiment, the polarization analyzing structure 16 is a variable analyzer.

There are many possible embodiments of a variable analyzer 16, for example it could be a rotating linear polarizer, a combination of a linear polarizer with a liquid crystal variable retarder, or it could be a linear polarizer with a rotating quarter wave plate to generate a plurality of polarization states for measurements. In some other embodiments, the polarization analyzing structure 16 could also be a polarization beamsplitter, with two branches of detection systems for each polarization branch. With a variable analyzer 16, the recorded irradiance values of different analyzer polarization states could be compared and analyzed and the effect of the iris scattered light could be minimized.

More preferably, the polarization analyzing structure 16 could be moved out of the optical path for some measurements like corneal topography. Experiments demonstrate that with linear cross polarizers in the illumination and detection systems, the recorded ocular surface image will present a pattern of the iris reflected light coupled with corneal birefringence, and a dark cross-shaped pattern or two separate dark hyperbolic arcs are observed, which are usually referred to as the "isogyre" patterns, and the isogyre pattern corresponds to the part where the polarization state of the incident light is almost unchanged after the cornea-iris-cornea reflected light pathway. In the corneal periphery, a series of colored quadrangular rings with rounded corners are presented, which are referred to as the "isochrome" rings. This is partly because the cornea retardance variation increases from the corneal center to the corneal periphery. If parallel linear polarizers are used in the illumination and detection systems, the recorded images present a complementary bright "isogyre" pattern to the previous case of cross polarizers, and a different set (a complementary set) of isochrome rings are recorded. When circular polarizers, instead of linear polarizers, are used, no isogyre patterns are present, but the isochrome rings at the corneal periphery are still present. Further, the ocular surface reflection will flip the handedness of the circular polarized incident light. When there is no polarization analyzing structure 16 in the optical path, the recorded images will not present conical birefringence, i.e. neither isogyres, nor isochrome patterns are present, which will simplify the corneal topography retrieval and improve measurement accuracy.

Figure 2:
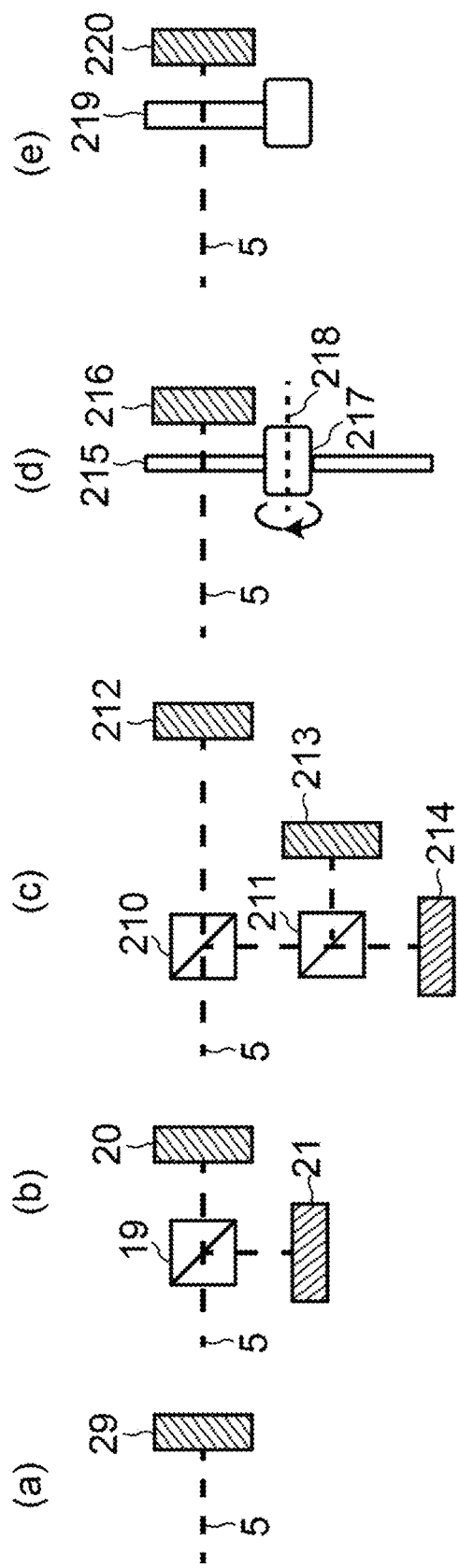
FIG. 2 presents five embodiments of the detection system.

FIG. 2 presents five embodiments of the detection system 8. FIG. 2(*a*) shows one embodiment of a single multispectral detector 29, with respect to the optical axis 5 of the imaging system. 29 has pixels covering both visible and infrared spectra. Narrow band spectral filters are matched to each pixel in 29 to differentiate multiple spectral bands. For example, the detector 29 could have four different types of pixels: red (R), green (G), blue (B) and near infrared (NIR) pixels. In FIG. 2(*b*), the detection system comprises a dichroic beamsplitter 19, and two different detectors 20 and 21, as previously shown in FIG. 1. In FIG. 2(*c*), the detection system comprises a first dichroic beamsplitter 210, which splits light into a visible branch and an infrared branch. A detector 212 is responsive to the visible branch. A second dichroic beamsplitter 211 further splits the infrared branch into a first infrared (IR1) branch and a second infrared (IR2) branch, and corresponding detectors 213 and 214 are used to match the two branches. The embodiment of the beamsplitter in FIG. 2(*b*) and FIG. 2(*c*) could be a cube beamsplitter, a plate beamsplitter, a pellicle beamsplitter, etc.

In FIG. 2(*d*), the detection system comprises a rotating spectral filter wheel 215, which has different narrow band spectral filters embedded inside. A motor 217 rotates around an axis 218, and the narrow band spectral filters in front of a detector 216 change in a cyclic order. The detector 216 is sensitive to a broad range of spectrum including visible and infrared. In one embodiment, the alternating narrow band spectral filters in the filter wheel 215 are of R, G, B, NIR four types.

In FIG. 2(*e*), a tunable spectral filter 219 is placed in front of a detector 220 in a hyperspectral setup. 219 is used to select different wavelengths to pass onto 220. The embodiment of the tunable spectral filter could be a liquid crystal tunable filter, or an acousto-optic tunable filter, etc.

The detection systems in FIG. 2(*d*) and FIG. 2(*e*) are spectral scanning detectors, which form images of two-dimensional object at a narrow spectral range at any moment, and the wavelength is sequentially adjusted to cover a broad spectral range, including the visible and infrared spectra, to generate multispectral or hyperspectral image series of the object.

Figure 3:
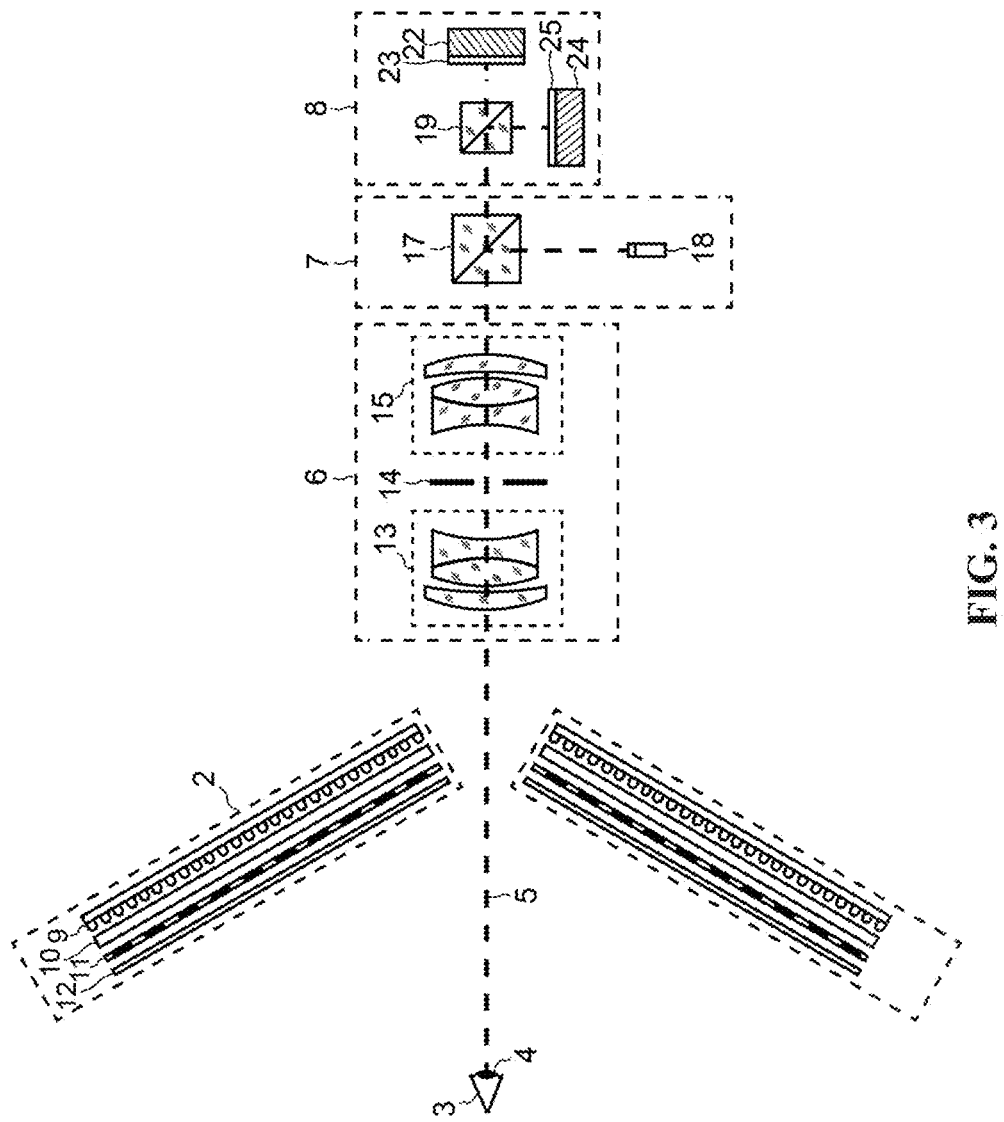
FIG. 3 presents another embodiment of a multispectral ocular surface evaluator with polarization image sensors in the detection system.

FIG. 3 presents another embodiment of a multispectral ocular surface evaluator, similar to the embodiment in FIG. 1. However, in FIG. 3, the polarization analyzing structure is located in the detection system 8, instead of the imaging system 6. The detection system 8 comprises detectors with polarization image sensors, and the polarization analyzing structure is fabricated on chip in the detection system as an analyzer layer 23 on a detector 22, and an analyzer layer 25 on a detector 24. One preferred embodiment of the polarization image sensor to work in the visible and near infrared spectra is Sony IMX250MZR/MYR or Sony IMX253MZR/MYR sensor, and the Sony polarization image sensors have four different directional polarizers (0°, 45°, 90°, and 135°) in each pixel block. By comparing and combining the images from different analyzers in each frame, the polarimetric information could be used to reveal ocular properties, such as the tear film lipid layer thickness, etc. For corneal topography measurements, images of orthogonal analyzer polarizations, for example, 0° and 90° could be combined to minimize the effect of corneal birefringence.

Note that in some embodiments, the imaging system 6 in FIG. 1 or FIG. 3 could also be a zoom lens system with continuously variable magnification.

Figure 4:
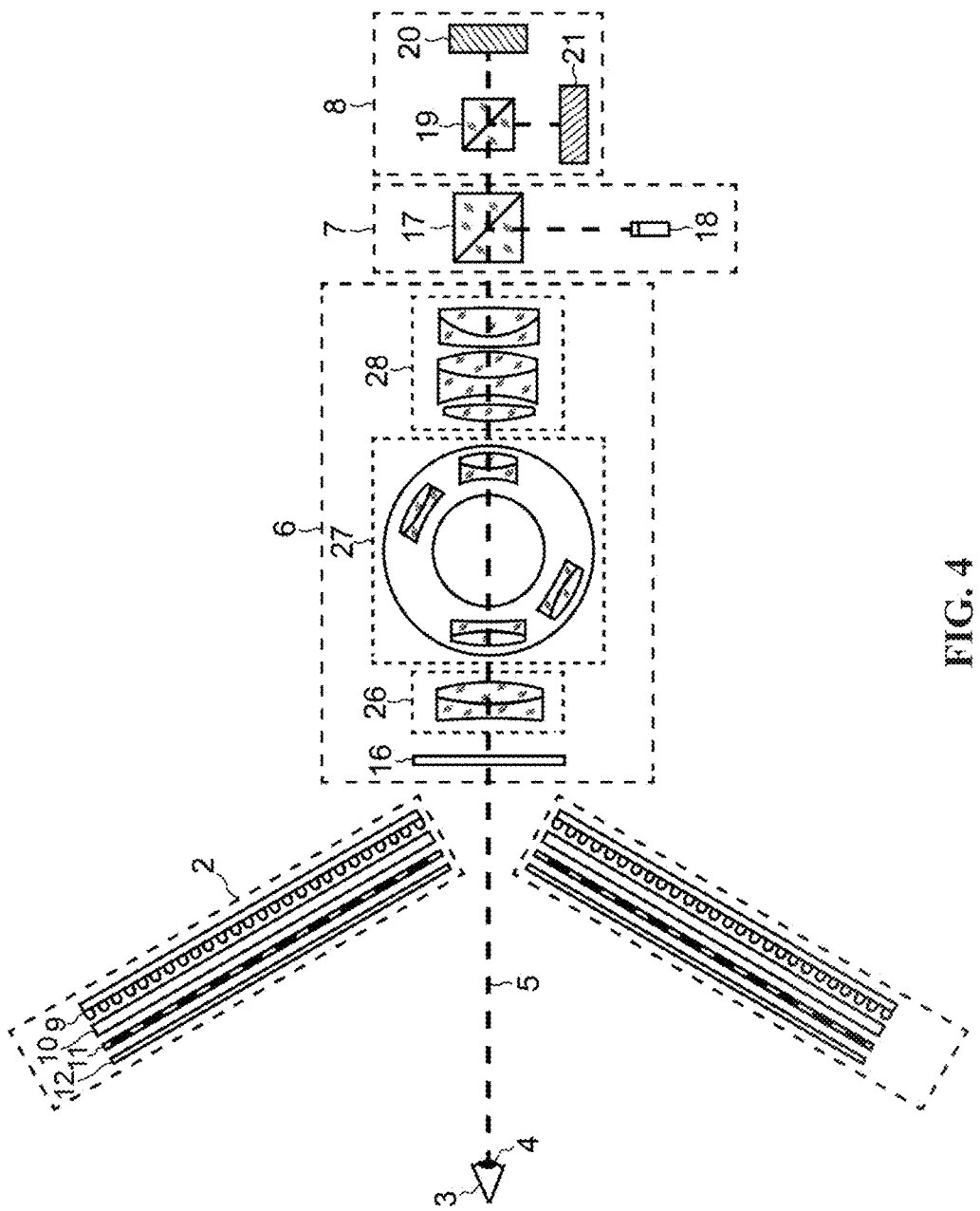
FIG. 4 presents another embodiment of a multispectral ocular surface evaluator with a magnification changer.

FIG. 4 presents another embodiment of a multispectral ocular surface evaluator. The illumination system 2, the eye alignment system 7, and the detection system 8 are similar to that in FIG. 1. However, the imaging system 6 in FIG. 4 comprises an objective lens group 26, a magnification changer 27 and a focusing lens group 28. Preferably, the objective lens group 26 turns the input light into collimated beams. The magnification changer 27 follows the objective lens group 26. The magnification changer 27 enables the ocular surface evaluator to image a relatively large area at a low magnification to evaluate bulbar redness, and image meibomian glands, etc., and image small ocular features at a high magnification to evaluate tear meniscus height, bases of eyelashes, meibomian gland orifices, etc. In one embodiment, the magnification changer 27 are stepwise, such as different sets of rotatable telescopes that can be flipped in and out of the optical path as shown in FIG. 4, and one preferred embodiment of the telescope for the magnification changer is a Galilean telescope. In some embodiments, the magnification changer 27 is an afocal zoom lens group, and the magnification could be adjusted continuously. Similar to FIG. 1, a polarization analyzing structure 16 could be placed either in the imaging system 6 or the detection system 8, and preferably it's a variable analyzer.

Figure 5:
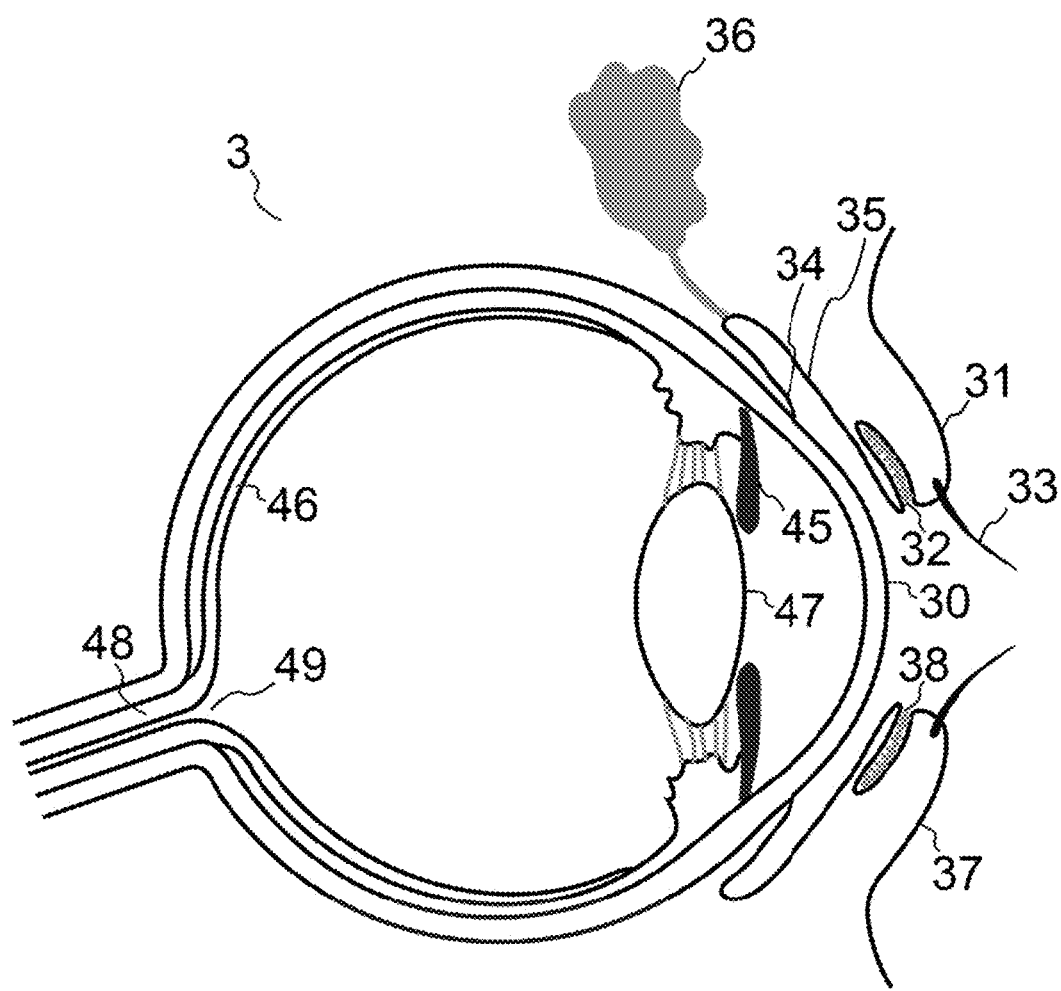
FIG. 5 presents the anatomical structures of an eye.

FIG. 5 presents the anatomical structures of an eye 3. Cornea 30 is protected by an upper eyelid 31 and a lower eyelid 37. The conjunctiva comprises bulbar conjunctiva 34 and palpebral conjunctiva 35. 34 and 35 form a conjunctival sac, which serves as a tear reservoir. Meibomian glands 32 are embedded in the tarsal plate of the upper eyelid 31, and the base of eyelashes 33 are anterior to the meibomian glands 32. Similarly, meibomian glands 38 are embedded in the lower eyelid 37. A lacrimal gland 36 is located at the upper lateral region of each orbit, and the secretory ducts of the lacrimal gland 36 directs aqueous tears to the ocular surface and forms the aqueous layer of the tear film. The iris 45 is anterior to the lens 47. The retina 46 is connected to the optic nerve 48 which transmits visual signals from the retina to the brain. The optic nerve head (or the optic disc) 49 is the exit where the ganglion cell axons leaving the eye.

Figure 6:
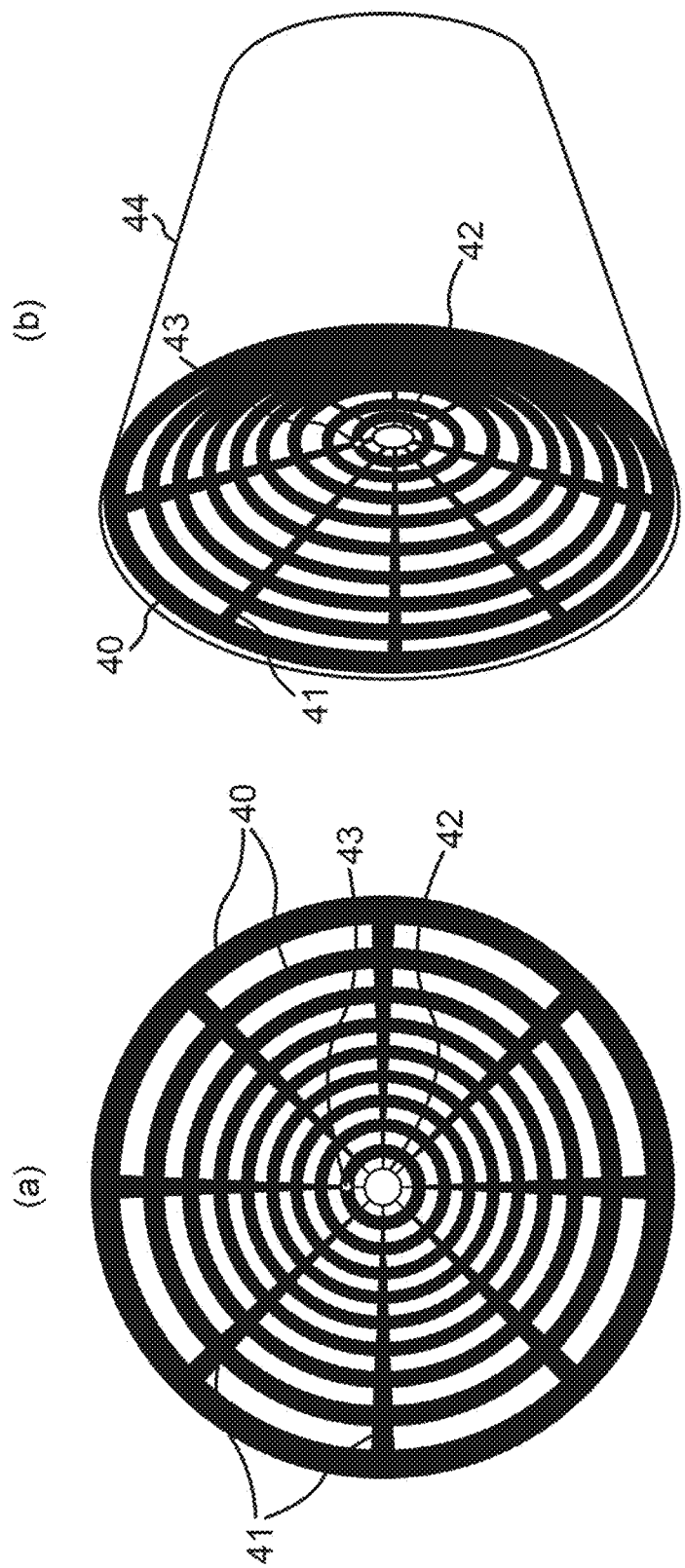
FIG. 6 presents one embodiment of the projection pattern of the illumination system with a front view and a side view.

FIG. 6 presents one preferred embodiment of the projection pattern of the illumination system. FIG. 6(a) is a front view, and FIG. 6(b) is a side view. The projection pattern comprises concentric rings 40 and radial spokes 41. The projector has a central aperture 42 in the posterior end to allow reflected light off the ocular surface to pass through to be collected by the imaging system. A micro thermal camera 43 is optionally embedded in the illumination system, to measure a dynamical thermal change of the ocular surface. 43 operates in long wavelength infrared (LWIR), typically in the wavelength range of 7.5 µm to 14 µm. Preferably, the thermal camera aperture on the illumination system has a diameter of smaller than 15 mm. One embodiment of the micro thermal camera is the FLIR Lepton micro thermal camera (FLIR Systems, Wilsonville, Oreg.). The micro thermal camera is placed paraxially with the imaging system. The exterior package 44 of the ocular surface evaluator provides mechanical support and protection of the system.

Figure 7:
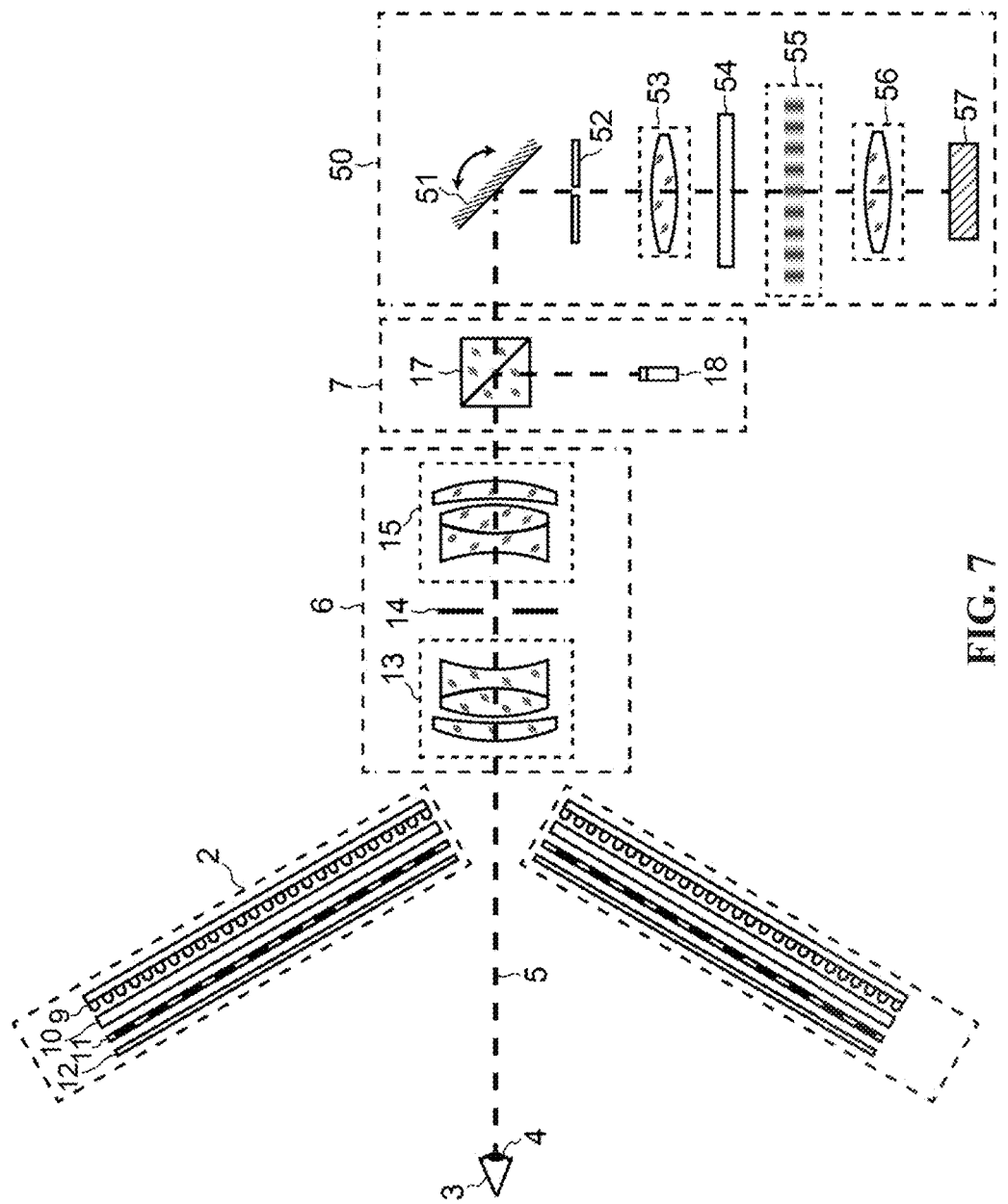
FIG. 7 presents one embodiment of a hyperspectral ocular surface evaluator with a transmissive spectrometer system.

FIG. 7 presents one embodiment of a hyperspectral ocular surface evaluator with a transmissive spectrometer system. The illumination system 2, the imaging system 6 and the eye alignment system 7 are similar to that in FIG. 3. The detection system in FIG. 7 is a transmissive spectrometer system 50. Inside 50, a rotary scanning mirror 51 guides light through a slit 52. One preferred embodiment of the rotary scanning mirror 51 is a rotating polygon mirror. Preferably, the slit is located at the intermediate image plane formed by the preceding imaging system 6 and the eye alignment system 7. The slit 52 spatially filters out one spatial dimension to avoid overlap of dispersed beams from two spatial dimensions. Light from the slit 52 passes through a collimating lens group 53, and the collimated light passes through a polarization analyzing structure 54, before reaching a transmission grating 55. Preferably, the polarization analyzing structure 54 could be removed out of the optical path for some measurements. The embodiment of the transmission grating 55 could be a volume phase holographic (VPH) transmission grating, a diffractive lens, a prism, a Bragg grating, or other similar dispersive optical elements. After the transmission grating 55, the collimated incoming light is dispersed into different output angles for different wavelengths, and the dispersed light passes through a focusing lens group 56 and reaches a detector 57. The embodiment of the detector 57 could be a charge-coupled device (CCD), a complementary metal-oxide-semiconductor (CMOS), or other functionally similar imaging recording devices. Each image detected contains one slice of the object spread out in the perpendicular dimension for different spectral channels. Typically, hundreds of spectral channels are used in the detector. After rotating the scanning mirror 51, the two-dimensional object image could be obtained.

Figure 8:
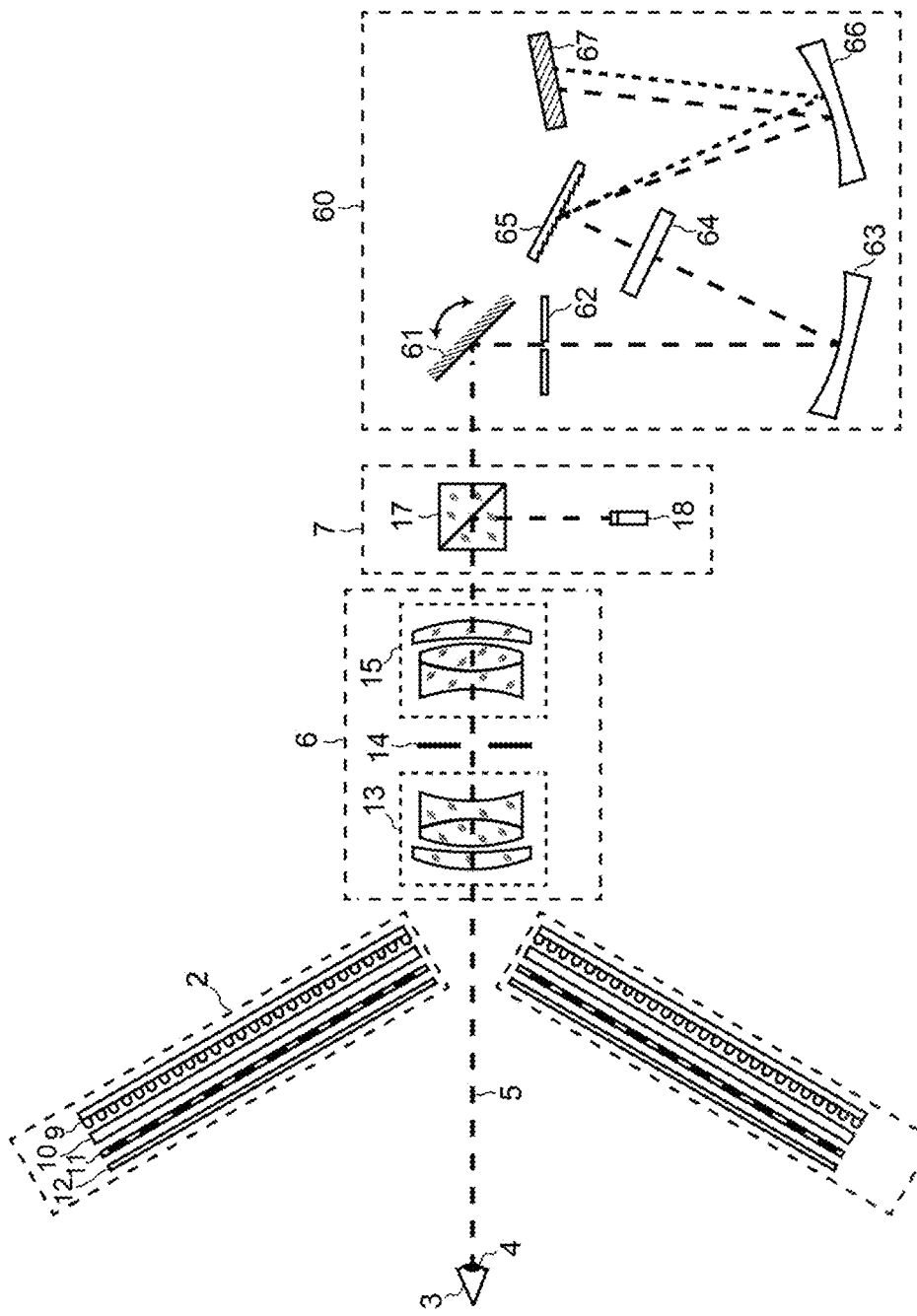
FIG. 8 presents one embodiment of a hyperspectral ocular surface evaluator with a reflective spectrometer system.

FIG. 8 presents one embodiment of a hyperspectral ocular surface evaluator with a reflective spectrometer system. The illumination system 2, the imaging system 6 and the eye alignment system 7 are similar to that in FIG. 7. The detection system in FIG. 8 is a reflective spectrometer system 60, comprises a rotary scanning mirror 61, a slit 62, a collimating mirror 63, a polarization analyzing structure 64, a grating 65, a focusing mirror 66 and a detector 67. In a preferred embodiment, the scanning mirror 61 is a rotating polygon mirror, and the slit 62 is located at the intermediate image plane formed by the preceding optics. Collimated light off 63 passes the polarization analyzing structure 64. Preferably, the polarization analyzing structure 64 could be removed out of the optical path for some measurements. The grating 65 could be a reflective diffraction grating, a holographic grating or other dispersive optical elements. The detector 67 could be a CCD or a CMOS, or other recording devices. In some embodiments, 67 is a detection system including multiple detectors and dichroic beamsplitters, for example, 67 could comprise two detectors, one for visible and NIR (VNIR) spectrum, and the other for short wave infrared (SWIR) spectrum, with a dichroic mirror to split the incoming light into VNIR and SWIR two branches.

Preferably, the polarization analyzing structure 54 in FIG. 7 and 64 in FIG. 8 is a variable analyzer, and the embodiments of the variable analyzer include a linear polarizer mounted in a rotary wheel, or a combination of a linear polarizer and a rotating quarter wave plate or a liquid crystal variable retarder, etc. Preferably, the polarization state of the polarization analyzing structure 54 or 64 alters after the rotary mirror 51 or 61 finishes each scanning cycle.

Note that in some embodiments, the scanning mirror 51 in FIG. 7 and 61 in FIG. 8 could also be other scanning system, such as a point-scanning whiskbroom scanner, and the detection spectrometers are adjusted accordingly.

A Fourier transform spectrometer could also be used as the spectrometer system. The spectrum of the object is obtained from the Fourier transform of interferograms. One embodiment of the Fourier transform spectrometer is based on a Michaelson interferometer, which contains one moving mirror and one stationary mirror. The optical path difference (OPD) is modulated by the displacement of the moving mirror, so that the detected signal varies with the moving mirror displacement.

Furthermore, in some embodiments, spectral scanning methods which capture the two-dimensional spatial image of a narrow spectral band (quasi-monochromatic image) in a single frame, and step through the spectral range during scanning could also be employed in multispectral and hyperspectral ocular surface evaluator. These spectral scanning methods could employ spectral filters in the form of rotating narrow band spectral filters, acousto-optic tunable filters, and liquid crystal tunable filters, etc. These filters could be placed on either the illumination side as a monochromator or on the detection side as a spectral scanning detector.

Moreover, in some embodiments, instead of using a scanning system for the detection system, a snapshot imaging spectrometer system, such as a computed tomography imaging spectrometer (CTIS), an image mapping spectrometer (IMS), etc. could be employed as the detection system. For example, in a CTIS detection setup, a field stop could be used to limit the intermediate image formed by the preceding optical elements, and a collimating lens converts each field point into a collimated beam incident on a computer generated hologram (CGH), which disperses the incident light into a spectral range with different directions, an imaging lens collects all spectral images on the same detector, to form all spectral images in a single frame, with high order images of the different spectral images overlapping with each other.

Figure 9:
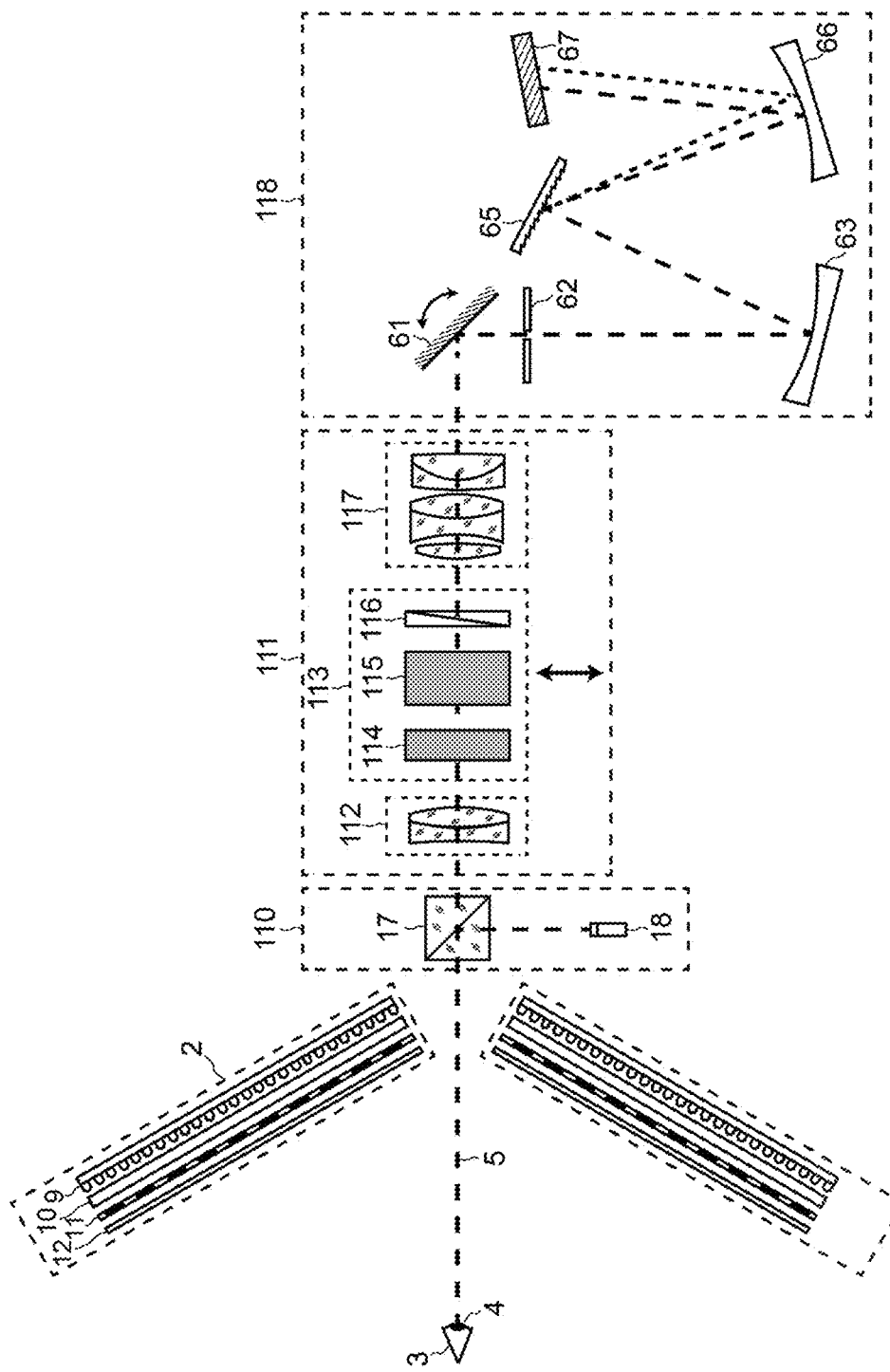
FIG. 9 presents an embodiment of an ophthalmic spectropolarimeter with two high order retarders.

FIG. 9 presents an embodiment of an ophthalmic spectropolarimeter with high order retarders. The illumination system 2, the eye alignment system 110, and the spectrometer system 118 are similar to those in FIG. 8. The imaging system 111 comprises an objective lens group 112, a polarization analyzing structure 113, and a focusing lens group 117. The polarization analyzing structure 113 introduces spectral carriers to the input light. Preferably, light after the objective lens group 112 is collimated, before entering 113. One embodiment of the polarization analyzing structure 113, comprises a first birefringent plate 114, a second birefringent plate 115 and a linear polarizer 116. 114 and 115 are two optically thick (high order) retarders such that the retardance of either birefringent plate varies significantly with wavenumber. Preferably, the first birefringent plate 114 has its fast and slow axes aligned with the horizontal and vertical directions, respectively. The second birefringent plate 115 has its fast and slow axes aligned at 45° and −45°, respectively. The linear polarizer 116 is aligned with the fast axis of 114.

Note that the polarization analyzing structure 113 could be displaced out of the optical path of the system for some functionalities. For example, 113 could be inserted into optical path for tear film lipid layer thickness measurements, and moved out of the optical path for corneal topography measurements. The position of 112 and 117 could be adjusted accordingly to compensate for the total optical path length variation.

Applying Mueller calculus to the cascading optics of the polarization analyzing structure 113, the irradiance is $$I(\sigma)=(½)S_0(\sigma)+(½)S_1(\sigma)\cos[\delta_2(\sigma)]+(½)S_2(\sigma)\sin[\delta_2(\sigma)]\sin[\delta_1(\sigma)]-(½)S_3(\sigma)\sin[\delta_2(\sigma)]\cos[\delta_1(\sigma)], \quad (1)$$

where $[S_0, S_1, S_2, S_3]^T$ is the Stokes vector of the ocular surface reflected light incident onto 113, $\delta_1(\sigma)$ and $\delta_2(\sigma)$ are the phase retardation of 114 and 115, respectively:

$$\delta_1(\sigma)=2\pi d_1\Delta n_1\sigma, \delta_2(\sigma)=2\pi d_2\Delta n_2\sigma \quad (2)$$

where $d_1$ and $d_2$ are the thicknesses of the two birefringent plates 114 and 115, respectively. Birefringence values $\Delta n_1$ and $\Delta n_2$ are the corresponding differences in refractive indices of the ordinary and extraordinary rays. Note that if the material dispersion is small, the birefringence $\Delta n$ is almost constant, the phase retardation is almost linearly proportional to the wavenumber $\sigma=1/\lambda$, and the terms in Eq. (1) are quasi-sinusoidal functions of $\sigma$.

Rearrange Eq. (1) to obtain $$I(\sigma)=(½)S_0(\sigma)+(¼)S_1(\sigma)[\exp(i\delta_2)+\exp(-i\delta_2)]-(⅛)[S_2(\sigma)-iS_3(\sigma)]\exp[i(\delta_1+\delta_2)]+(⅛)[S_2(\sigma)-iS_3(\sigma)]\exp[i(\delta_1-\delta_2)]+(⅛)[S_2(\sigma)+iS_3(\sigma)]\exp[i(\delta_2-\delta_1)]-(⅛)[S_2(\sigma)+iS_3(\sigma)]\exp[-i(\delta_1+\delta_2] \quad (3)$$

The inverse Fourier transform of Eq. (3) gives the autocorrelation function, which will enable the retrieval of the full Stokes vector components.

Note that the polarization analyzing structure 113 obviates the necessity of a variable analyzer, as was described in the previous embodiments of this invention. Since such an embodiment allows retrieval of full four components of the Stokes vector of the reflected light, the depolarized portion of the iris scattered light would lower the degree of polarization $(S_1^2+S_2^2+S_3^2)^{1/2}/S_0$, but won't affect the relative ratio of $S_1$, $S_2$, and $S_3$. The effect of the polarized portion of the iris scattered light could be further minimized with additional measurements of corneal birefringence to enhance instrument accuracy for tear film measurements.

Figure 10:
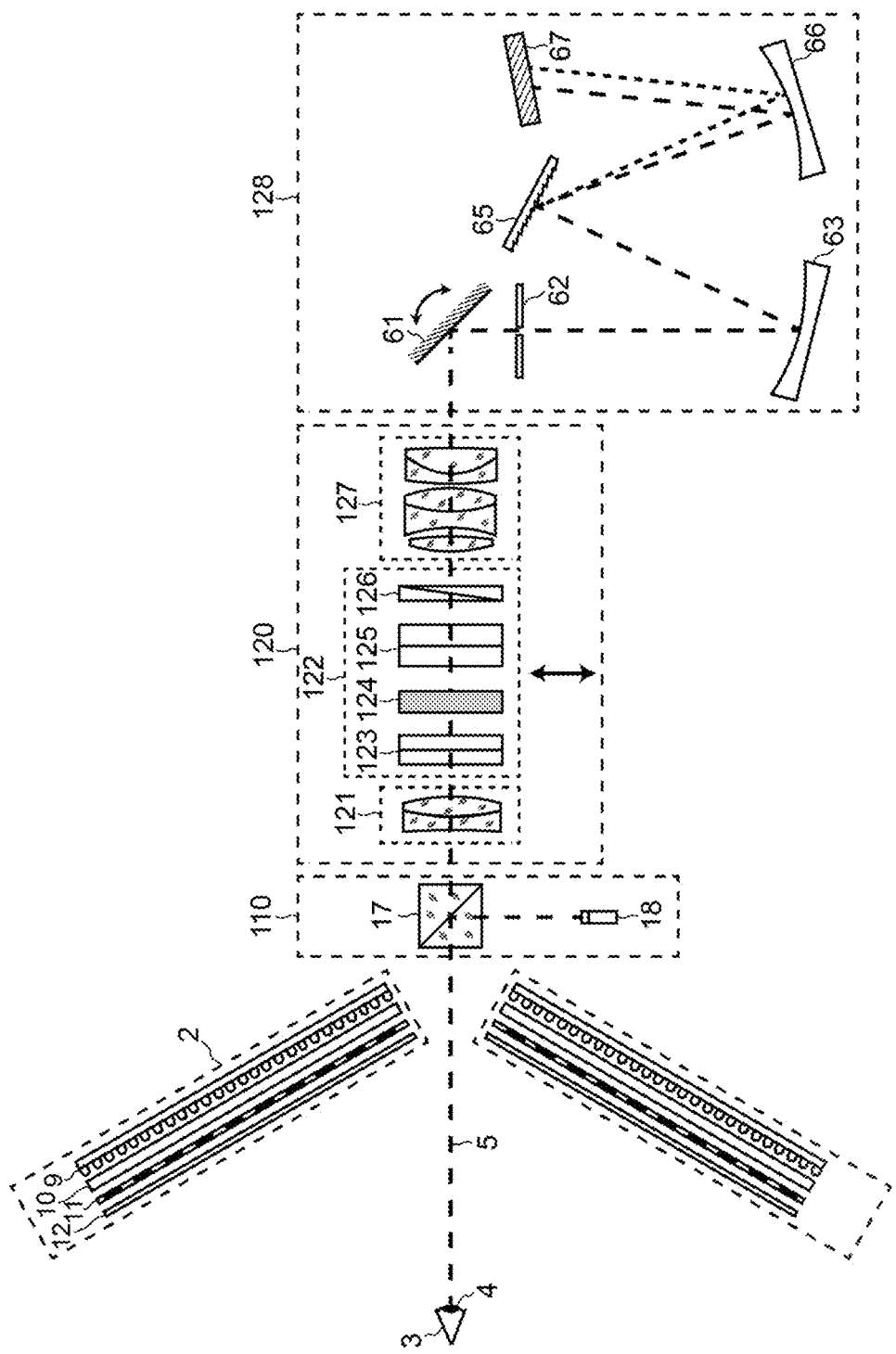
FIG. 10 presents an embodiment of an ophthalmic spectropolarimeter with two Savart plates.

FIG. 10 presents an embodiment of an ophthalmic spectropolarimeter with Savart plates. The illumination system 2, the eye alignment system 110, and the spectrometer system 128 are similar to those in FIG. 8. The imaging system 120 comprises an objective lens group 121, a polarization analyzing structure 122, and a focusing lens group 127. The polarization analyzing structure 122 introduces spatial carriers to the input light. Preferably, light after the objective lens group 121 is collimated before entering 122. One embodiment of the polarization analyzing structure 122 comprises a first Savart plate 123, a broadband half wave plate 124, a second Savart plate 125, and an analyzer 126. Either of the two Savart plates 123 and 125 consists of two equal thickness uniaxial crystal subplates such that the optic axes of both subplates are aligned at 45° to the surface normal and rotated 90° with respect to each other. Preferably, the broadband half wave plate 124 is made of polymers.

Applying Mueller calculus to 122, the irradiance is $$I(x,y)=(½)S_0(x,y)+(½)S_2(x,y)\cos(2\pi U_2 y)-(¼)|S_{13}(x,y)|\cos\{2\pi(U_2-U_1)y-\arg[S_{13}(x,y)]\}+(¼)|S_{13}(x,y)|\cos\{2\pi(U_2+U_1)y+\arg[S_{13}(x,y)]\} \quad (4)$$

where $$S_{13}(x,y)=S_1(x,y)+iS_3(x,y), \quad (5)$$

and $U_1$ and $U_2$ are the spatial carrier frequencies introduced by the first and second Savart plates.

In some other embodiments, the polarization analyzing structure 122 comprises two achromatic birefringent prism pairs of different thicknesses and an analyzer.

Similar to FIG. 9, the polarization analyzing structure 122 could be displaced out of the optical path of the system for some functionalities. The position of 121 and 127 could be adjusted accordingly to compensate for the total optical path length variation.

Note that in any system where the Savart plates are used, their thickness values have to be properly selected to make sure that the optical path differences of the sheared beams are within the coherence length of the light source, otherwise, the detected fringes will be of very low contrast or even entirely washed out, which will hamper subsequent polarization analysis.

Figure 11:
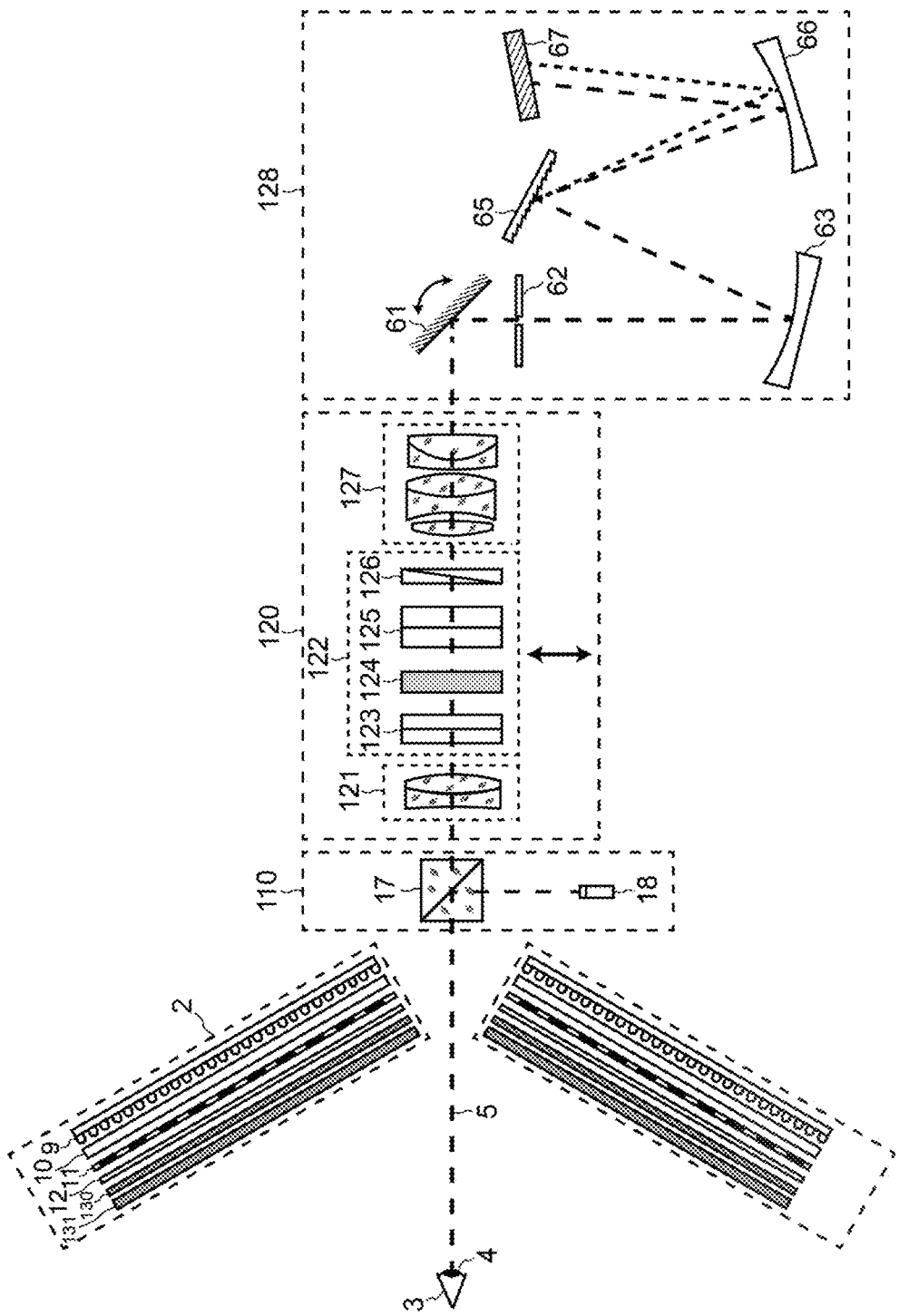
FIG. 11 presents another embodiment of an ophthalmic spectropolarimeter with two high order retarders in the illuminator system, and two Savart plates in the imaging system.

FIG. 11 presents yet another embodiment of an ophthalmic spectropolarimeter. Anterior to the structures 9 to 12, the illumination projector additionally comprises two high order retarders: a first birefringent film 130, and a second birefringent film 131. These two additional birefringent films 130 and 131 are preferably made of polymers that can conform to the shape of the illumination system 2, and they introduce spectral carriers to the incident light onto the ocular surface. The eye alignment system 110, the imaging system 120 and the spectrometer system 128 are similar to those in FIG. 10. One embodiment of the projection pattern panel 11 in FIG. 11 could be a panel of zones with different polarization states, instead of zones of different transparency or color.

Because of the added carriers both before and after the ocular surface in FIG. 11, not only the Stokes vector of the ocular surface reflected light, but the Mueller matrix of the ocular surface could be characterized with this layout.

Figure 12:
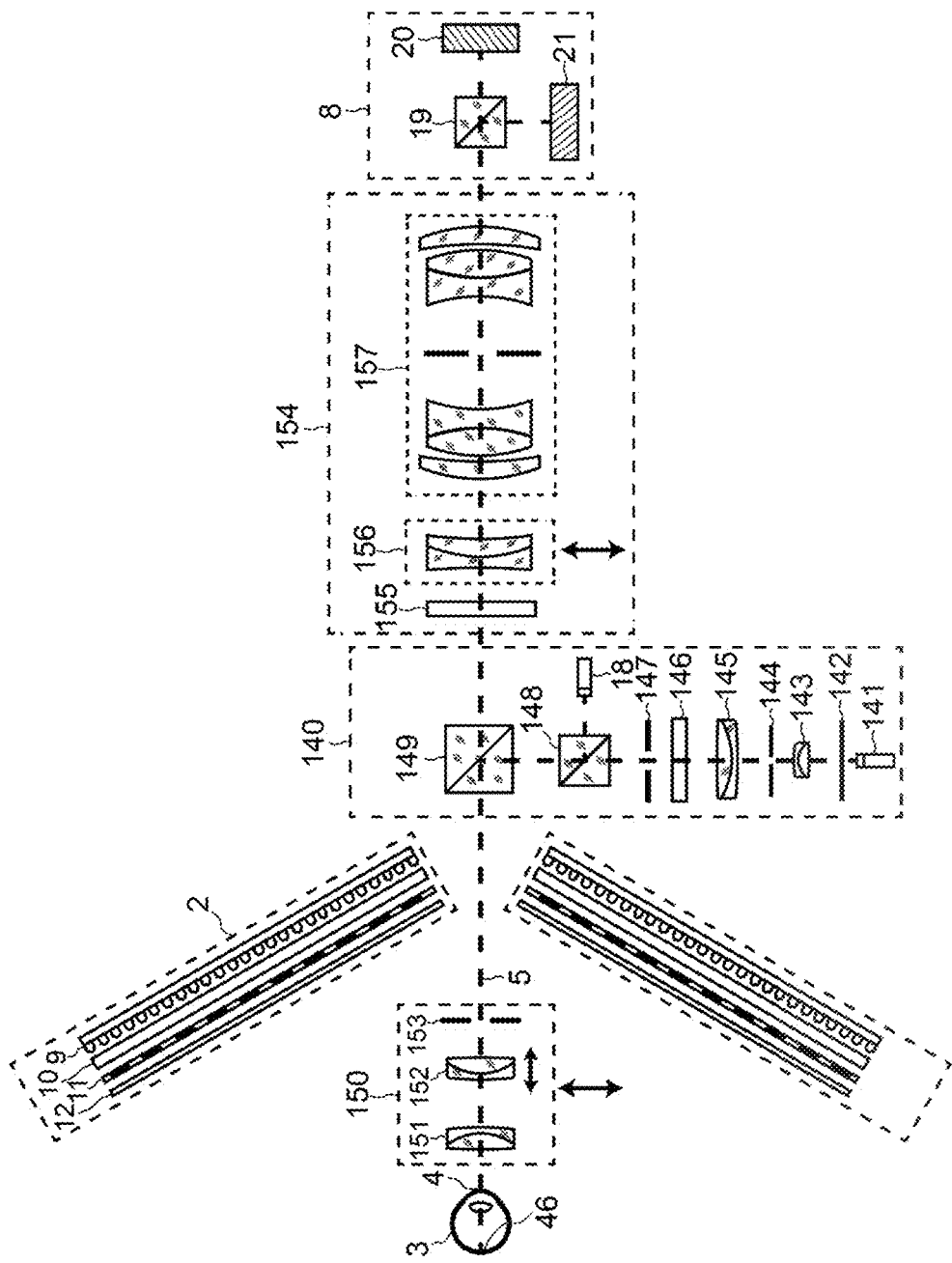
FIG. 12 presents one embodiment which incorporates a retinal polarimeter to measure the corneal birefringence.

FIG. 12 presents one embodiment of the ocular surface evaluator, which incorporates a retinal polarimeter to measure the corneal birefringence. This setup comprises a polarimetric fundus camera, and the corneal birefringence is retrieved by using the radial symmetry of the retinal Henle's fiber layer. The ocular surface illumination system 2 is turned off during the corneal birefringence measurement with the retinal polarimeter. The retinal illumination optics comprise 140 and 150. 140 is located in a fixed position in the device, while 150 is removable from the optical path. The fixed illumination part 140 is a combination of the eye alignment system and part of the retinal polarimeter. 140 comprises a light source 141, which preferably is a laser or laser diode, a neutral density filter 142, an illumination focusing lens 143, a spatial filter or a pinhole 144, an illumination collimating lens 145, a variable polarizer 146, an illumination entrance pupil 147, a beamsplitter 148 and a corresponding eye alignment light source 18, and another beamsplitter 149. When the system is used for retinal polarimeter measurements, 18 is turned off, and 141 is turned on. While for other measurements, 141 is turned off and 18 is turned on for eye alignment. There are many embodiments of the variable polarizer 146, including a combination of a linear polarizer with a liquid crystal variable retarder, or a linear polarizer with a rotating quarter wave plate, etc. to generate a plurality of input polarization states for measurements.

Figure 13:
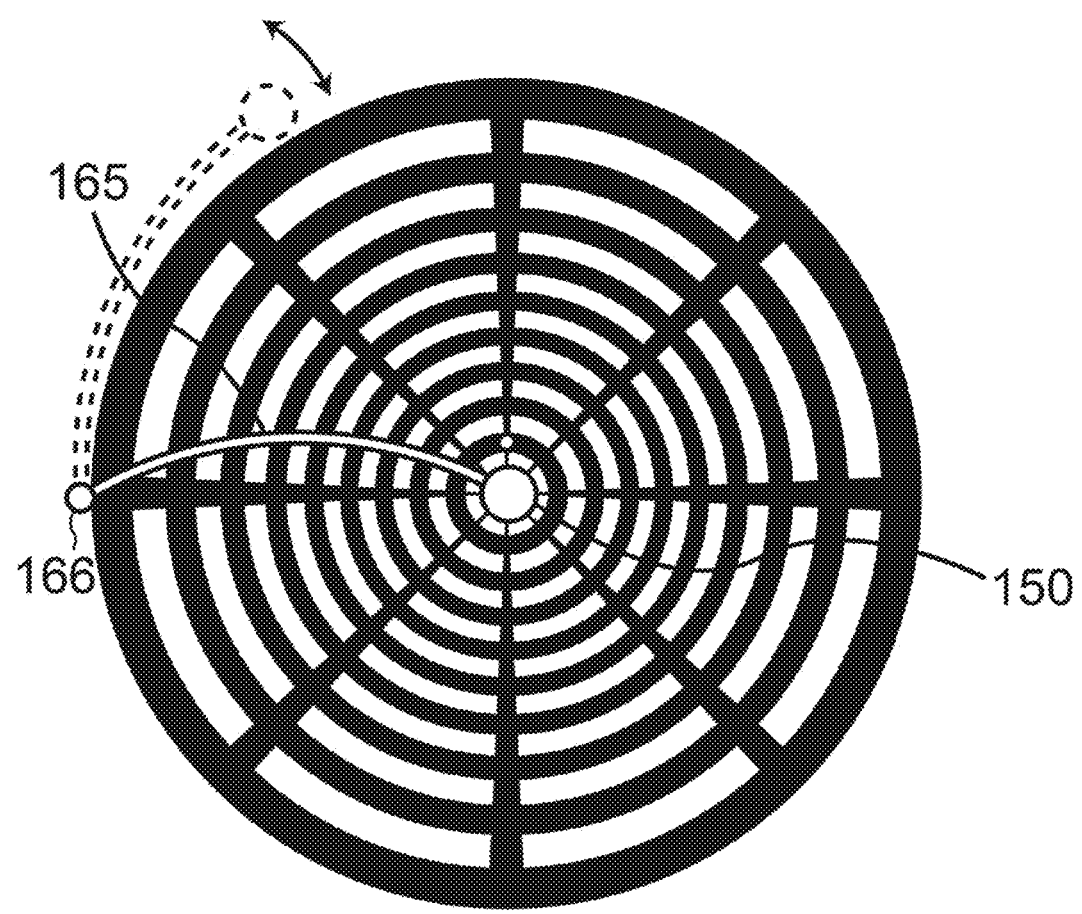
FIG. 13 presents a removable illumination part for retinal polarimetry with an arced arm.

The removable illumination part 150 for retinal polarimetry is placed in an arced arm 165 conforming to the shape of the edge of the illumination system 2 as shown in FIG. 13. The arced arm 165 can be rotated around a pivot 166. Preferably there is a mechanical rotation lock, which aligns 150 with the optical axis 5 of the rest of the optical system.

In FIG. 12, 150 comprises a first lens 151, a second lens 152 and a pupil 153. For an emmetropic eye, 151 and 152 form an afocal system, and the collimated illumination light reflected from the beamsplitter 149 is focused on the retina. For an ametropic eye, one of the lenses in 150, either 151 or 152 is adjusted along the optical axis 5 to compensate for the defocus refractive error of the subject, such that the dot image of the illumination source 141 on the retina of the subject is smallest and sharpest. Correspondingly, 150 departs from an afocal system after defocus adjustment for ametropia. The pupil 153 controls the amount of the reflected light from the retina 46 that can enter into the imaging system.

Reflected light from the retina 46 passes through 150 and becomes collimated again before passing through the beamsplitter 149. After 149, light passes through an imaging system 154, which comprises a variable analyzer 155. Similar to the variable polarizer 146, there are many possible embodiments of 155. A removable compensating lens group 156 is inserted into the optical path for the retinal polarimeter to match the optics of 150. In the setup in FIG. 12, the removable compensating lens group 156 is a negative lens group. The imaging lens group 157 is used to image the ocular surface 4 on the image plane of the detection system 8 without the insertion of 150 and 156. In the retinal polarimeter setup, 156 has to be inserted to match the optics of 150 so that the imaging lens group 157 could still be used. Note that with the insertion of 150 and 156, the detector image plane is no longer conjugate to the ocular surface 4, but to the retina 46. Preferably, there are baffles and stray light blockers placed appropriately in the imaging system 154 to block and reduce the amount of stray light that can reach the detector image plane.

Note that the lens group 150 is shared in both the illumination and imaging paths. The lens surface reflection of 150 is a main source of stray light that has to be managed carefully to maintain enough signal to noise ratio of the retinal image due to the weak retinal reflection. To reduce the lens surfaces in lens group 150, in some other embodiments, only one objective lens is used for retinal polarimeter, and the defocus adjusting lens group is incorporated in the removable compensating lens group 156.

By adjusting the variable polarizer 146 and the variable analyzer 155, sixteen independent measurements of the birefringence of the eye could be measured so that the entire Mueller matrix of the eye could be calculated. The birefringence of the eye includes the corneal birefringence and the retinal birefringence.

Note that for the retinal polarimeter setup, the light source 141 could be a quasi-monochromatic laser source, so that the multispectral and hyperspectral spectral channels are not fully used and somewhat redundant. But the light source 141 could also be a supercontinuum laser with a broad spectrum, so that different spectropolarimetric properties of the eye could be quantified. If a supercontinuum laser is used, the detection system could be matched with a spectrometer system as that shown in FIG. 7 or FIG. 8.

If the pupil of subject is large enough, potentially dilated with a mydriatic drop, it's possible to image not only the macula but the optic nerve head 49 as well with the retinal polarimeter, hence the retinal nerve fiber layer thickness could also be measured.

Figure 14:
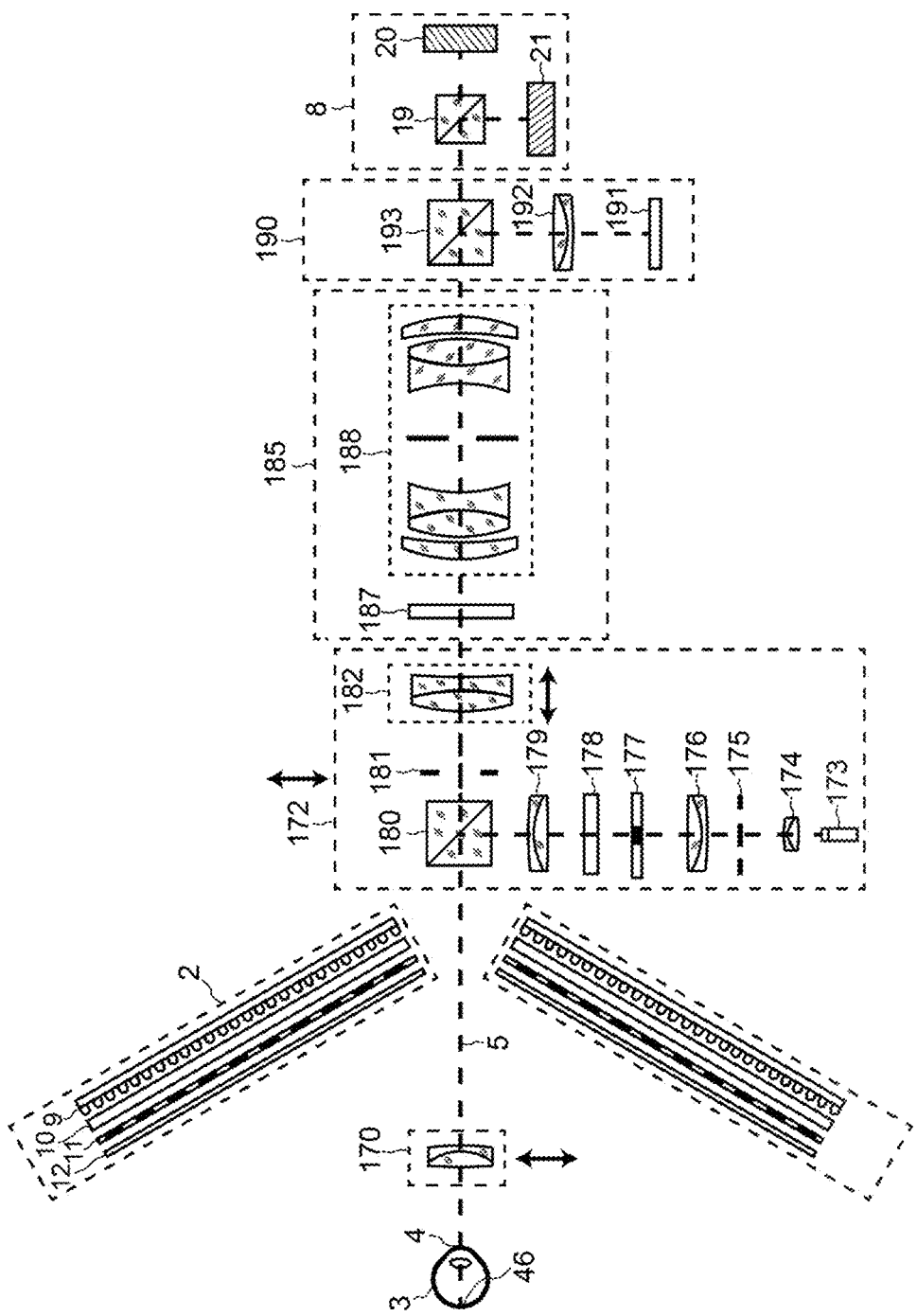
FIG. 14 presents another embodiment of the ocular surface evaluator with a retinal polarimeter.

FIG. 14 presents another embodiment of the ocular surface evaluator with a retinal polarimeter. The illumination system 2, the imaging system 185, the eye alignment system 190, and the detection system 8 are used to image the ocular surface 4 of the eye 3. The imaging system 185 comprises a variable analyzer 187, and an imaging lens group 188. The eye alignment system 190 is used for fixation of the eye, which comprise a microdisplay 191, a lens group 192, and a beamsplitter 193. The microdisplay 191 could display a fixation dot in the center along the optical axis if the ocular surface is under measurement, it could also displace the position of the fixation dot to help image different parts of the fundus, for example, the optic nerve head 49. The microdisplay 191 is conjugate to the retina 46.

To measure the corneal birefringence with a retinal polarimeter, an objective lens group 170 and a removable optics group 172 are inserted into the optical path of the system. 172 comprises a retinal illumination light source 173, a condenser lens group 174, an annular aperture 175 for illumination control, a collimating lens group 176, a black dot 177, a variable polarizer 178, a relay lens group 179, a beamsplitter 180, an aperture 181 and a compensating lens group 182. The annular aperture 175 is conjugate to the center of the beamsplitter 180, which is further conjugate to the pupil of the eye. 175 is also conjugate to the illumination light source 173. Hence an annular shaped illumination path is formed on the cornea to avoid corneal back reflection, while providing sufficient light on the retina 46. The black dot 177 is conjugate to a plane between the front surface and the back surface of 170 to avoid the back reflection of the objective lens 170, and the size of the black dot is chosen such that back reflection from both the front and back surfaces of 170 are blocked. This is critical since 170 is shared in both the illumination and imaging paths. The retinal illumination optics include 170, and 173-180. The compensating lens group 182 is adjustable along the optical axis 5, which is used to compensate the defocus refractive error of the subject under measurement.

Figure 15:
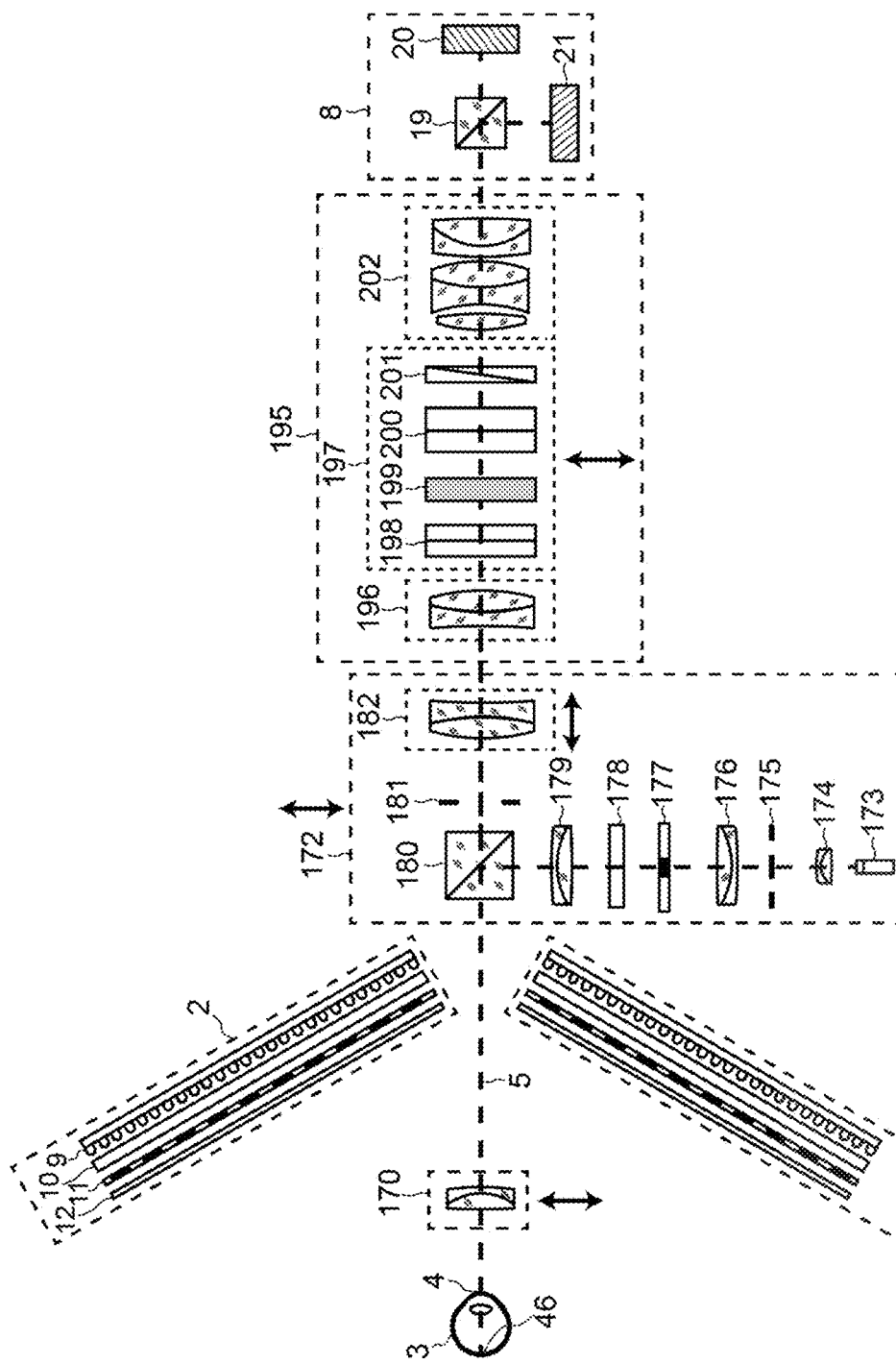
FIG. 15 presents another embodiment of the ocular surface evaluator with a retinal polarimeter with two Savart plates.

FIG. 15 presents another embodiment of the ocular surface evaluator with a retinal polarimeter. The illumination system 2, the objective 170 and the removable optics group 172 are similar to those in FIG. 14. The imaging system 195 is similar to 120 of FIG. 11. The imaging system 195 comprises a lens group 196, a polarization analyzing structure 197, and a focusing lens group 202. The polarization analyzing structure 197 introduces spatial carriers to the input light. Preferably, light after the lens group 196 is collimated, before entering 197. One embodiment of the polarization analyzing structure 197 comprises a first Savart plate 198, a broadband half wave plate 199, a second Savart plate 200, and an analyzer 201. The detection system 8 could be a multispectral system as shown in FIG. 15 or a hyperspectral system.

Further, the retinal polarimeter could also use a scanning laser as the illumination source.

Note that although in the preferred embodiments, the multispectral or hyperspectral ocular surface evaluator works in the visible and near infrared spectra, it could also be readily extended to work in the short-wave infrared (SWIR), mid-wave infrared (MWIR), and ultraviolet (UV) spectrum as well.

After being recorded by the detection system, the images are digitally processed. Depending on the features or parameters of clinical interest, the digital processing steps of the recorded images may vary. However, in general, the digital processing comprises steps of image preprocessing, feature extraction, parameter estimation, etc.

Image preprocessing includes the steps to calibrate the irradiance reflectance with reference samples. For the corneal reflectance calibration, a reference sample of a known optical material (for example, BK7 glass), with the radius of curvature close to that of an average human cornea could be used. For meibography, a reference white target, such as a Spectralon white diffuse reflectance target could be used. Image preprocessing further includes image smoothing, contrast enhancement, and removal of uneven illumination, etc. Image smoothing could be done using median filters of a properly chosen size or other smoothing algorithms. Contrast enhancement, or contrast stretch, includes multiple transform methods in both spatial domain and spectral domain. Spatial contrast enhancement methods include stretching the original data number range to fill the full gray level range, with linear, nonlinear, histogram equalization, reference stretch and other related methods. Spectral contrast enhancement methods include normalization stretch, spatial domain blending, etc. Removal of uneven illumination could be partly done with the reflectance calibration, and partly done with a high-pass filter or a homomorphic filter.

Feature extraction aims to reduce the original data dimensionality and obtain the most important subset of the original data to extract relevant feature information of the ocular surface and adjacent structures. Similar procedures could be applied to both multispectral and hyperspectral ocular surface imaging, although it's especially useful for hyperspectral ocular surface imaging due to its high spectral dimensionality. Feature extraction is not an absolutely necessary step for some applications. Commonly used feature extraction methods include principal component analysis (PCA), minimum noise fraction (MNF), independent component analysis (ICA), spectral angle mapper (SAM) and spectral information divergence (SID), etc.

Parameter estimation is the step to retrieve key clinical parameters from the recorded images. Due to the multifunctional nature of the ocular surface evaluator, various clinical parameters are estimated with different methods. Parameter estimation is especially important for a hyperspectral ocular surface evaluator, as described in detail later in this invention.

After key parameters are estimated, the final evaluation of a certain aspect of the ocular surface health could be reported either completely automatically based on digital results, or further analyzed by a medical professional.

In the preferred setup for the corneal topography measurement, the subject is positioned properly and requested to fixate on the alignment light source to align the eye with the instrument. Light from the illumination projector is directed toward the eye of the subject, and the reflected images are collected into the imaging system and recorded. The setup geometry, the reflected image pattern and the corresponding magnification are used to calculate the geometrical shape of the cornea to generate a corneal topography map.

Tear breakup time (TBUT) is evaluated in this invention by measuring the time interval immediately after a blink and the occurrence of a disrupted or distorted spot or area of the grid or ring pattern of the reflected images of the illumination projector off the ocular surface. Usually, a series of blink intervals are recorded, the TBUT is analyzed for each blink, and a statistical result of TBUT is reported.

Tear meniscus height (TMH) in his invention is evaluated by recording an image of the lower eyelid margin with the tear meniscus. The TMH is calculated based on the magnification. If the magnification is adjustable with a magnification changer or a zoom lens group, it's preferred to use a high magnification for TMH measurement.

Bulbar redness can be evaluated by selecting certain areas of the exposed bulbar conjunctiva in a recorded image of the ocular surface as the region of interest (ROI). The ROI could be a line, an arc or a small area within the bulbar conjunctiva. The number of blood vessels, blood vessel width distribution, the ratio of the area of blood vessel versus that of the total region of interest, or other degree-of-redness parameters could be evaluated to quantify bulbar redness. Similarly, hyperemia of palpebral conjunctiva can also be quantitatively evaluated by imaging everted eyelids and analyzing the palpebral redness.

Meibography with direct illumination could be done using the disclosed device by taking images of the inner surface of the everted upper or lower eyelids. Preferably, only part of the illumination light sources within a relatively uniform subsection of the illumination projector (for example, within a single ring of a concentric ring pattern) is used for meibography to avoid potential noise caused by the illumination pattern. The meibomian glands morphology and distribution could be best revealed in the infrared spectrum, however, the visible spectrum could be used to reveal the vascular distribution within the same region, and multispectral image fusion might be helpful to diagnose meibomitis, since increased vascularity close to the meibomian glands orifices might indicate meibomitis.

In a multispectral setup, quantitative indices such as the "Difference Meibomian Gland Index" (DMGI), $$DMGI = |R_r - R_n| \tag{6}$$

and the "Normalized Difference Meibomian Gland Index" (NDMGI), $$NDMGI = |R_r - R_n|/|R_r + R_n| \tag{7}$$

could be used to enhance the contrast of the meibomian glands with respect to neighboring tissues, $R_r$ and $R_n$ are the irradiance reflectance values of the red and near infrared color channels calculated at each pixel.

Images of the meibomian gland orifices and eyelashes could also be used for ocular examination to reveal potential clogging by solidified lipids, or potential crusting at the base of the eyelashes due to blepharitis, etc.

In the prior art, the lipid layer thickness is evaluated by inspecting the reflected colors off the cornea, due to the interference of multiple reflections at the air-lipid layer-aqueous layer interface, and the lipid layer thickness is determined by the color match in the visible spectrum, which usually is evaluated in red, green and blue three color channels. In this invention, multispectral or hyperspectral reflectance values in many more spectral channels in both visible and infrared spectra are used for lipid thickness and refractive index retrieval. Further, polarization change of the light before and after the reflection off an ocular surface could be used to model the air-lipid layer-aqueous layer three layer interface, and the lipid layer thickness could be extracted based on the method of spectropolarimetry, which combines imaging spectroscopy with polarimetry, and could enable nanometer-level lipid thickness resolution. The additional spectral channels further enable unique lipid thickness measurement within a much larger thickness range, without any ambiguity. The background of iris-scattered light could be reduced by mutual subtraction of different polarization setups, and the partially polarized background scattering induced by iris could be further minimized with measurement results of corneal birefringence, which significantly improves the lipid layer measurement accuracy, since the iris background noise is a limiting factor for tear film lipid layer thickness measurement methods described in the prior art.

An optional micro thermal camera 43 in FIG. 6 is employed to characterize the thermal dynamics of the ocular surface. The thermal camera is placed at a small aperture close to the central aperture for the main imaging system and operates in the LWIR wavelength range of about 7.5 to 14 µm. Even though the LWIR micro thermal camera and the visible-NIR optical system are not coaxial, they are arranged to be paraxial in this invention so that simultaneous measurement of the tear film evolution and thermal dynamical profile of the ocular surface is possible. Further, with properly chosen magnification and field of view of the micro thermal camera, it could enable direct characterization of the thermal profile of the ocular surface and the connection of the tear break up and the ocular surface thermal dynamics.

In some embodiments, the ocular surface evaluator incorporates a retinal polarimeter, which could evaluate the corneal birefringence. If some portion of the central cornea is used for analysis, the cornea could be approximately modeled as a uniform linear retarder with a fixed phase retardance and a fixed slow axis orientation. The retinal Henle's layer could be modeled as a uniform linear retarder with a fixed phase retardance and a radial slow axis distribution with the fovea at the center. The combination of the two birefringent structures will generate a bow-tie pattern, widely observed clinically. Based on the radial slow axis distribution of the Henle's fiber layer in the macula, the corneal birefringence could be calculated with the "bowtie" method. Alternatively, a "screen" method could be used to derive corneal birefringence, which utilize the fact that the retinal phase retardance is significantly smaller that the corneal phase retardance in the macula, hence the corneal phase retardance and slow axis orientation could be retrieved by simply averaging over an area around the macula. The corneal phase retardance and slow axis distribution indicate the biomechanical structure of the transparent cornea, and is useful for inspection after refractive surgeries. Further, the retinal polarimeter could also be used to quantify the retinal nerve fiber layer (RNFL) thickness. The thinning of the RNFL thickness could help to diagnose and monitor the progression of glaucoma.

In the following, a detailed analysis procedure for a hyperspectral ocular surface evaluator is described. Its rich spectral and spatial information might reveal physiological properties of the cornea and adjacent structures, mainly the eyelid and sclera. These ocular tissues are all modeled as multi-layer structures, with each layer described with characterization parameters, such as collagen concentration, water volume fraction, etc. A forward model based on physics and physiology selects key characterization parameters for each layer, and an inverse model is used to estimate the parameters. The inverse model could be a parametric method, or a non-parametric machine learning method.

Next, a generalized mathematical framework for the forward and inverse model are described. The mathematical framework could be applied to the ocular surface and adnexal tissues, including the cornea, the sclera and the eyelid.

Figure 17:
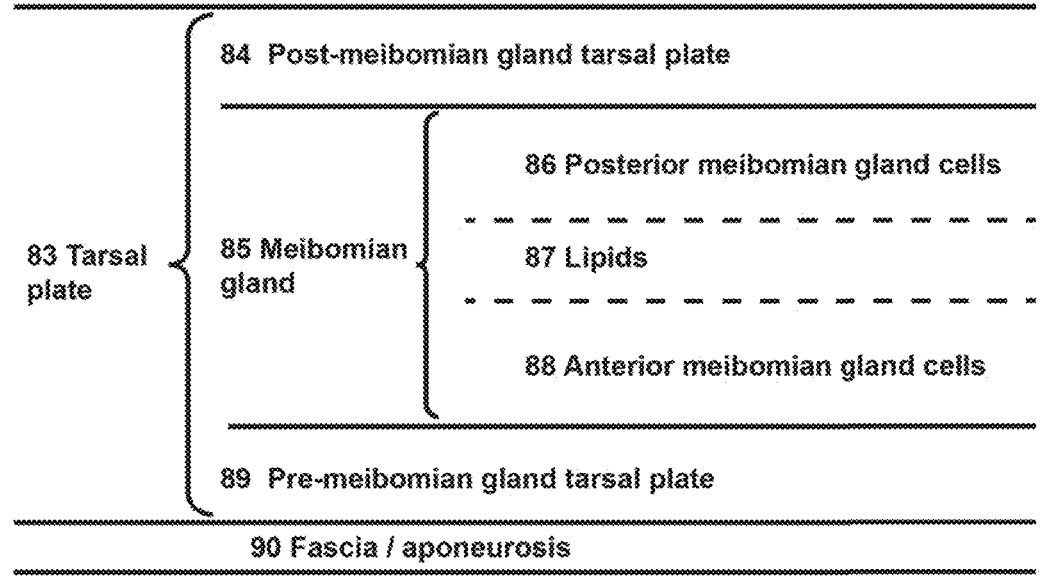
FIG. 17 presents one multilayer model of an everted eyelid.

The multilayer structures of an ocular surface, an everted eyelid, and a sclera in the forward model are shown in FIGS. 16, 17, and 18, respectively. FIG. 16 presents a multilayer model of an ocular surface (including cornea and tear film) in the forward model, comprises the tear film lipid layer 70, the tear film aqueous layer 71, the tear film mucous layer 72, the corneal epithelium 73, the Bowman's layer 74, the conical stroma 75, the Descemet's membrane 76, the corneal endothelium 77, the aqueous humor 78, the iris 79 and the lens 80.

FIG. 17 illustrates a multilayer everted eyelid model. The layers of the eyelid are labeled from the conjunctival side above to the cutaneous side below in sequence: the conjunctival epithelium 81, the conjunctival stroma 82, the tarsal plate 83, the fascia or aponeurosis 90, the orbicularis oculi muscle 91, the hypodermis 92 of the eyelid, the dermis 93 of the eyelid, the living epidermis 94 of the eyelid, and the stratum corneum 95 of the epidermis of the eyelid. 90 is the fascia of the lower eyelid retractor or the levator aponeurosis of an upper eyelid. For the area of the everted eyelid that contains the meibomian gland, the tarsal plate could be further divided into the post-meibomian gland tarsal plate 84, the meibomian gland 85, and the pre-meibomian gland tarsal plate 89. The post-meibomian gland tarsal plate 84 includes the loose connective tissue. In the preferred method, the meibomian gland 85 is further divided into three sublayers, the posterior meibomian gland cells 86, the lipids or meibum 87, the anterior meibomian gland cells 88. For direct illumination on an everted eyelid, the structures beneath the tarsal plate 83 (90~95) contribute minimally to the reflected and back scatted images, and could be ignored, if the induced errors are acceptable.

FIG. 18 presents a multilayer model of a sclera, consisting of the conjunctiva 96, the Tenon's capsule 97, the episclera 98, the scleral stroma 99, and the lamina fusca 109.

Note that the above divisions of the layers and sublayers in FIG. 16 to FIG. 18 are meant to represent the core structures of the ocular surface and adnexal structures for optical modeling purposes, hence they are not exact anatomical representations. If necessary, each layer can be divided further into sublayers, and additional anatomical layers could be added. For example, the living epidermis 94 of an eyelid in FIG. 17 could be further divided into four sublayers: stratum basale, stratum spinosum, stratum granulosum, and stratum lucidum, from the dermis side to the stratum corneum side.

In the forward model, an input vector space of characterization parameters of the ocular surface and adnexal tissues is mapped to an output vector space of the spectral components of the hyperspectral ocular surface evaluating device, $$p \rightarrow x, x = f(p) \qquad (8)$$

$f$ is the forward mapping function, p is an input vector of ocular characterization parameters, and for each layer p comprises the concentration of core components and thickness values. For example, in a representative j-th layer in the model, $p_j=[p_{th}, p_{col}, p_{mel}, p_{car}, p_{bil}, p_{myo}, p_{lip}, p_w, p_{bld}, p_o]$, and each component of the vector $p_j$ is a scalar to characterize a certain feature, i.e. any k-th component $p_k \in \mathbb{R}^1$. $p_{th}$ is the layer thickness, $p_{col}$ is the collagen concentration in a layer, $p_{mel}$ is the melanin concentration, $p_{car}$ is the β-carotene concentration, $p_{bil}$ is the bilirubin concentration, $p_{myo}$ is the myosin concentration, $p_{lip}$ is the lipids concentration, $p_w$ is the water volume fraction, $p_{bld}$ is the blood volume fraction, $p_o$ is the oxygenation saturation. Preferably, only major components which will significantly affect the signal of the detection system are necessary to model each layer, hence the characterization parameters in different layers are different. For example, for a tear film lipid layer 70, only lipids thickness, and lipids refractive index are necessary, although the refractive index is wavelength-dependent. A series of these thicknesses, concentrations, etc., are modeled for each layer to form the input vector $p=[p_1, p_2, \ldots, p_j, \ldots, p_{end}]$, where $p_{end}$ is the last layer in a forward model.

x is the calibrated irradiance reflectance or the preprocessed data number of each spectral channel at a spatial point. $x=[x(\lambda_1), x(\lambda_2), \ldots, x(\lambda_{M-1}), x(\lambda_M)]$, and the subscript "M" is the total number of hyperspectral channels, and $x \in \mathbb{R}^M$.

Other relevant parameters, such as the concentration of elastin, actin, mucins, and other chromophores, could also be included in the model, and potentially could be more accurate, but on the other hand, the analysis with more parameters might be more complicated, noisier and more time-consuming. It's also preferred that the total number of parameters of all layers in the characterization vector p is smaller than the total number of spectral channels in the hyperspectral imaging system, in order to obtain robust regression. With this trade-off in mind, the choice of this forward model is aimed to quantify ocular surface and adnexal structures only with essential components.

The forward mapping p→x could be analyzed with a deterministic or stochastic model. The deterministic model of the transparent cornea could be based on Fresnel equations of optical transmission and reflection. The deterministic model of the non-transparent tissues, such as the eyelid or the sclera, could be a diffusion theory model, a radiative transfer model or a Kubelka-Munk (KM) theory model, etc. On the other hand, the most common stochastic model is a Monte-Carlo model.

As an example, a simplified mathematical model to retrieve the lipid layer thickness and refractive index based on spectropolarimetry is described herein. Based on the differences of refractive indices and biochemical components of adjacent layers, for the purpose of simplification in analysis yet without generating unacceptable errors, 71 to 78 in FIG. 16 could be simplified as a single optical layer. This is justified by the fact that the reflections at the interfaces between any two adjacent layers of 71 to 78, such as those at the mucous layer-corneal epithelium interface and the corneal endothelium-aqueous humor interface, are all less than 2% of the reflection at the air-lipid interface (in fact, most are at least two orders of magnitude less).

The air-lipid layer-aqueous layer forms a three-layer structure that contributes the most to the images of the ocular surface. The electric field reflectivity coefficients of the air-lipid layer interface based on Fresnel equations are $$r_1^p = \frac{n_1\cos\theta_0 - n_0\cos\theta_1}{n_1\cos\theta_0 + n_0\cos\theta_1}, r_1^s = \frac{n_0\cos\theta - n_1\cos\theta_1}{n_0\cos\theta_0 + n_1\cos\theta_1} \quad (9)$$

where $n_0$, $n_1$ are the refractive indices of air ($n_0=1$) and the lipids, $\theta_0$, $\theta_1$ are the incident angles in air and lipids, and p-polarization is parallel to the local plane of incidence, and s-polarization is perpendicular to the local plane of incidence.

Similarly, the electric field reflectivity coefficients of the lipid layer-aqueous layer interface are $$r_2^p = \frac{n_2\cos\theta_1 - n_1\cos\theta_2}{n_2\cos\theta_1 + n_1\cos\theta_2}, r_2^s = \frac{n_1\cos\theta_1 - n_2\cos\theta_2}{n_1\cos\theta_1 + n_2\cos\theta_2}, \quad (10)$$

where $n_2$, $\theta_2$ correspond to the aqueous layer.

Taking multiple reflections into account, the total reflectivities are $$R^p = \frac{r_1^p + r_2^p e^{-i2\beta}}{1 + r_1^p r_2^p e^{-i2\beta}}, R^s = \frac{r_1^s + r_2^s e^{-i2\beta}}{1 + r_1^s r_2^s e^{-i2\beta}} \quad (11)$$

The general form of Mueller calculus of the device is $$\vec{S}_{oq} = A_q I \Phi_2 R \Phi_1 \vec{S}_i, \quad (12)$$

where $\vec{S}_i$ is the Stokes vector of the incident light. $\Phi_1$ is a 4×4 rotation matrix that rotates the local input field components into the p and s polarization components of the point where the chief ray intersects on the ocular surface. R is a 4×4 reflection matrix in the local p and s coordinates. $\Phi_2$ is a 4×4 rotation matrix that rotates the reflected electric field of the chief ray from the local p and s coordinates of a point on the ocular surface to another coordinates system centered on the optical axis 5. I is a 4×4 matrix characterizing the polarization of the imaging system. $A_q$ is the q-th 4×4 matrix of the polarization analyzing structure. $\vec{S}_{oq}$ is the Stokes vector of the output light for the q-th polarization state of the polarization analyzing structure.

If a reference sample with known optical properties is used to calibrate the system, it's possible to simply Eq.(12) into the form of $$\vec{S}_{oq} = A_q I R \vec{S}_i \quad (13)$$

Preferably, the reference sample has a radius of curvature similar to that of the human cornea in order to minimize the calibration error.

Note that the above polarimetric analysis is valid for each individual spectral channel independently. However, applying the facts that the thickness of the lipid layer is fixed, and the refractive index of the lipid layer is a continuous, slowly varying function with wavelength could help reduce the error in the process of the thickness and refractive index retrieval.

The above analysis works relatively well for the portion of the ocular surface directly above the pupil. However, if an analysis of a larger area of the ocular surface including portions anterior to the iris is required, the iris reflected and scattered light has to be taken into account. Iris is rich in pigments; hence it absorbs part of the incident light regardless of the polarization state. The reflection and scattering of the iris is linked to its color, which is mainly determined by the structure of the iris stroma and the pigment distribution. The iris stroma contains collagen fibers, melanocytes, fibroblasts and clump cells. The anterior border layer of the iris is an uneven textured layer, which is a condensation of iris stroma. These structural features of the iris determine that the reflected light off the iris with fully polarized light incidence will become partially polarized.

Experimental tests demonstrate that the iris reflected light accounts for about 55% to 75% of the total detected irradiance, and this percentage variation is mainly due to the changes in the lipid layer thickness and the iris color. Further, preliminary experimental tests of the ocular surface with crossed polarizers in the illumination and detection path demonstrate that about 50% to 65% of the reflected light from the iris is polarized or statistically has a preferential polarization direction, and the percentage variation is dependent on the iris structure and its color. The rest about 35% to 50% of the iris reflected light is completely depolarized. The effect of the iris reflected light could be minimized by the mutual subtraction of detected irradiance values of the same point on the ocular surface under different polarization settings of the polarizer-analyzer pairs. However, this mutual subtraction to remove background noise is mostly effective only to the completely depolarized portion of the iris scattered light. Hence, a complete description of the corneal birefringence and a statistical analysis of the polarization state change of the iris reflection is necessary to more precisely model the ocular surface reflection.

The above analysis is for the cornea, which is a unique, transparent structure. To demonstrate the analysis of other non-transparent tissues, such as the everted eyelid and the sclera, a modified Kubelka-Munk theory model of the everted eyelid is described herein, those skilled in the art could readily extend the analysis to other types of models. The KM theory describes the resultant light from turbid materials with the irradiance transmittance ($t_n$) and reflectance ($r_n$) at each layer. Each layer is modeled as a homogenous layer of a material with a certain thickness that absorbs and scatters incident light. The irradiance transmittance $t_n(\lambda)$ and reflectance $r_n(\lambda)$ of the n-th layer are:

$$t_n(\lambda) = \frac{4\beta_n(\lambda)}{[1+\beta_n(\lambda)]^2 e^{K_n(\lambda)d_n} - [1-\beta_n(\lambda)]^2 e^{-K_n(\lambda)d_n}} \quad (14)$$

$$r_n(\lambda) = \frac{[1-\beta_n(\lambda)^2][e^{K_n(\lambda)d_n} - e^{-K_n(\lambda)d_n}]}{[1+\beta_n(\lambda)]^2 e^{K_n(\lambda)d_n} - [1-\beta_n(\lambda)]^2 e^{-K_n(\lambda)d_n}} \quad (15)$$

where $d_n$ is the thickness of the n-th layer, and $\beta_n(\lambda)$ and $K_n(\lambda)$ are $$\beta_n(\lambda) = \sqrt{A_n(\lambda)/[A_n(\lambda)+2S_n(\lambda)]} \quad (16)$$

$$K_n(\lambda) = \sqrt{A_n(\lambda)[A_n(\lambda)+2S_n(\lambda)]} \quad (17)$$

Further, the coefficients $A_n(\lambda)$ and $S_n(\lambda)$ are determined by the absorption coefficient $a_n(\lambda)$ and the reduced scattering coefficient $s_n'(\lambda)$ of each layer, and the final relations are dependent on the specific scattering and absorption properties of a material. In one preferred method, $$A_n(\lambda) = \frac{a_n(\lambda)}{\frac{1}{2}+\frac{1}{4}\left[1-\frac{s_n'(\lambda)}{s_n'(\lambda)+a_n(\lambda)}\right]} \quad (18)$$

$$S_n(\lambda) = \frac{s_n'(\lambda)}{\frac{4}{3}+\frac{38}{45}\left[1-\frac{s_n'(\lambda)}{s_n'(\lambda)+a_n(\lambda)}\right]} \quad (19)$$

Specifically, the absorption coefficient is dependent upon the chromophore types and concentrations in a layer. For example, in the top layer of an everted eyelid, the conjunctival epithelium 81, the absorption coefficient is modeled as $$a_1(\lambda) = p_{col\_1}a_{col}(\lambda) + p_{mel\_1}a_{mel}(\lambda) + p_{w\_1}a_w(\lambda) + p_{car\_1}a_{car}(\lambda) \quad (20)$$

where $a_{col}(\lambda)$, $a_{mel}(\lambda)$, $a_w(\lambda)$, and $a_{car}(\lambda)$ are the specific absorption coefficients of collagen, melanin, water, and β-carotene.

The absorption coefficient of the conjunctival stroma 82 could be modeled as $$a_2(\lambda) = p_{col\_2}a_{col}(\lambda) + p_{bld\_2}[p_{o\_2}a_{ohb}(\lambda) + (1-p_{o\_2})a_{dhb}(\lambda)] + (p_{w\_2}+0.9p_{bld\_2})a_w(\lambda) + p_{car\_2}a_{car}(\lambda) + p_{bil\_2}a_{bil}(\lambda) \quad (21)$$

where $a_{ohb}(\lambda)$, $a_{dhb}(\lambda)$, and $a_{bil}(\lambda)$ are the specific absorption coefficients of oxygenated hemoglobin, deoxygenated hemoglobin, and bilirubin. It also implicitly uses the fact that water is about 90% of the blood.

The absorption coefficient of the pre- and post-meibomian gland tarsal plate could each be modeled as a k-th layer with $$a_k(\lambda) = p_{col\_k}a_{col}(\lambda) + p_{bld\_k}[p_{o\_k}a_{ohb}(\lambda) + (1-p_{o\_k})a_{dhb}(\lambda)] + (p_{w\_k}+0.9p_{bld\_k})a_w(\lambda) + p_{car\_k}a_{car}(\lambda) + p_{bil\_k}a_{bil}(\lambda) + p_{myo\_k}a_{myo}(\lambda) \quad (22)$$

where $a_{myo}(\lambda)$ is the specific absorption coefficient of myosin, which is contained in the muscle of Riolan surrounding the meibomian glands.

Similar absorption coefficients could be derived for all the other layers with different chromophore distributions, and in general, $$a_n(\lambda) = \sum_{ch} p_{ch\_n}a_{ch}(\lambda) \quad (23)$$

where $p_{ch\_n}$ is the concentration of a type of chromophore in the n-th layer, and $a_{ch}(\lambda)$ is the specific absorption coefficient of that chromophore.

The reduced scattering coefficient of each layer is modeled with the form of $$s_n'(\lambda) = C_n\lambda^{-D_n} \quad (24)$$

where the parameters $C_n$ and $D_n$ are determined experimentally or adapted from the literature. Sometimes, $C_n$ is simplified to be linearly proportional to the collagen concentration $p_{col}$ of the n-th layer.

In the original Kubelka-Munk theory, surface reflection of the turbid material is neglected. To precisely evaluate the ocular surface and adnexal tissues, surface reflection has to be added into the model. At the interface of different layers, Fresnel equations could be used to model the irradiance transmittance and reflectance, in a lot of embodiments, the distance of the eyelid to the imaging system of the ocular surface evaluating device is much longer than the length of a meibomian gland, and the illumination could be approximated as normal incidence, and simplified Fresnel equations could be used. The irradiance transmittance $\tau_n(\lambda)$ and reflectance $\rho_n(\lambda)$ at the interface with normal incidence are $$\tau_n(\lambda) = \frac{4N_n(\lambda)N_{n+1}(\lambda)}{[N_{n+1}(\lambda)+N_n(\lambda)]^2} \quad (25)$$

$$\tau_n(\lambda) = \frac{4N_n(\lambda)^2}{[N_{n+1}(\lambda)+N_n(\lambda)]^2} \quad (25)$$

$$\rho_n(\lambda) = \left[\frac{N_{n+1}(\lambda) - N_n(\lambda)}{N_{n+1}(\lambda) + N_n(\lambda)}\right]^2 \quad (26)$$

where $N_n(\lambda)$ and $N_{n+1}(\lambda)$ are the refractive indices of the incident and transmitting layer.

If the incident angle is not negligible, the complete Fresnel equations could be used to derive irradiance transmittance and reflectance for oblique incident angles, and polarization states have to be taken into account.

Figure 19:
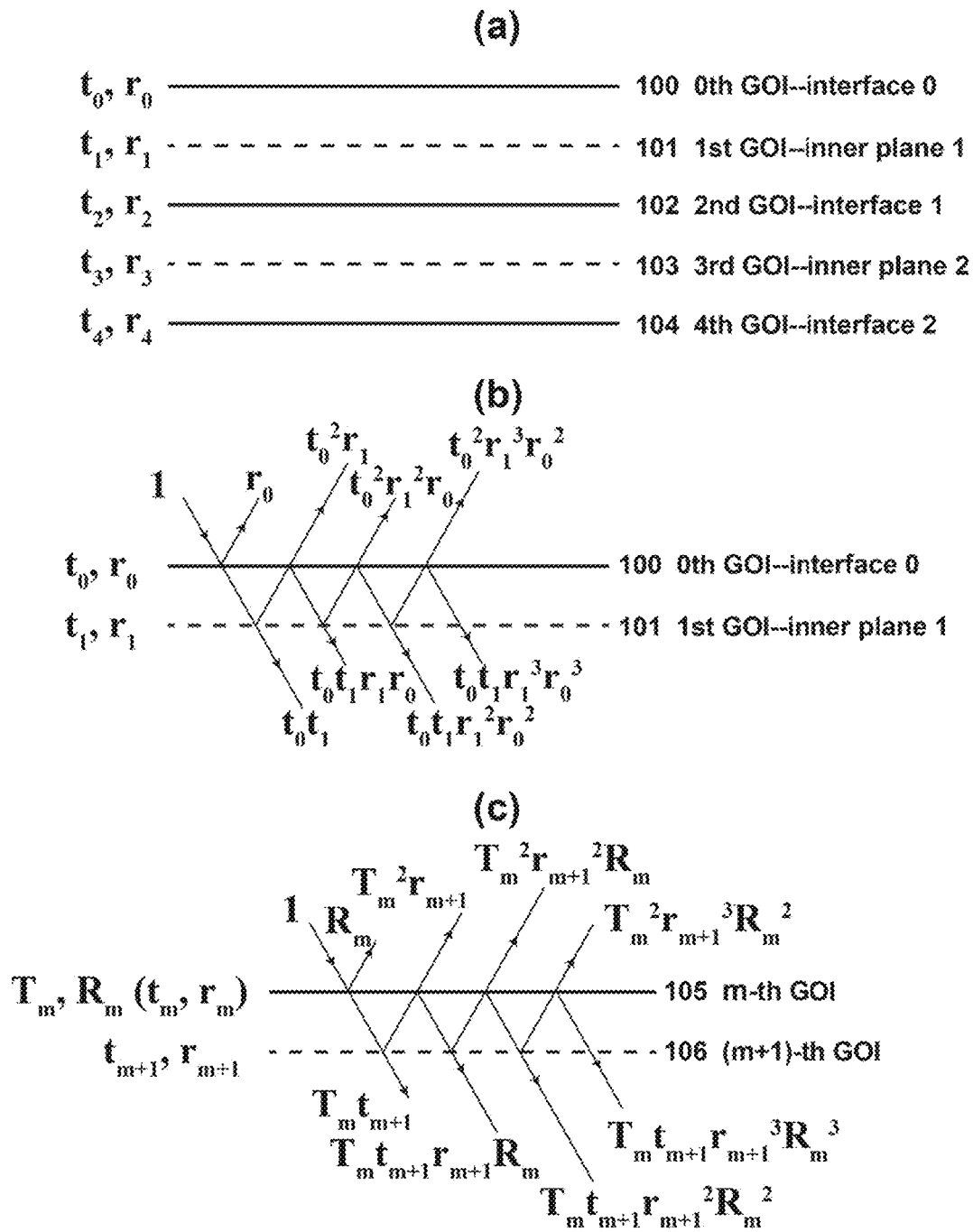
FIG. 19 presents multiple reflections between generalized optical interfaces.

In the modified KM theory model in this invention, multiple reflections between two adjacent layers and interfaces are taken into account. As shown in FIG. 19, after the calculation of the transmittance and reflectance of each layer with the KM theory, the net effect of the n-th layer could be modeled as if the transmission and reflection happen at a single plane, the n-th inner plane, representing each layer. Because of the material of each layer is turbid or translucent, the reflected light will add incoherently, thus the phase factors can be dropped and the exact location of the inner plane doesn't matter, as long as it's within the thickness of each layer. With this novel abstraction, each layer can be simplified as an optical plane analogous to an optical interface. Both the true optical interface and the abstracted optical interface of each layer could be referred to as the "generalized optical interface" (GOI). Hence, we get M=2n+1 generalized optical interfaces in total, with n inner planes from n layers, and n+1 interfaces forming the boundaries of the n layers. The transmittance and reflectance of each generalized optical interface are denoted as $t_m$ and $r_m$. If the m-th GOI is an inner plane, $t_m$ and $r_m$ are calculated as Eqs. (14) and (15), if the m-th GOI is an optical interface, $t_m$ and $r_m$ are calculated as $\tau_n$ and $\rho_n$ in Eqs. (25) and (26). In FIG. 19(b), starting with the first two generalized optical interfaces, which are the interface 0 and the inner plane 1, the total reflectance and transmittance after multiple reflections in between these two layers are:

$$R_1 = r_0 + t_0^2 r_1 \sum_{k=0}^{\infty} (r_1 r_0)^k = r_0 + \frac{t_0^2 r_1}{1 - r_1 r_0} \quad (27)$$

$$T_1 = t_0 t_1 \sum_{k=0}^{\infty} (r_1 r_0)^k = \frac{t_0 t_1}{1 - r_1 r_0} \quad (28)$$

$R_1$, $T_1$ could be viewed as the net effect of the first two generalized optical interfaces, and be used in multiple reflections calculation with the next GOI. Hence, an iteration process could be used to calculate the total reflectance and transmittance. In general, $R_{m+1}$, $T_{m+1}$ could be calculated from $R_m$, $T_m$ of all the previously analyzed interfaces, and $r_{m+1}$, $t_{m+1}$ of the (m+1)-th generalized optical interface:

$$R_{m+1} = R_m + \frac{T_m^2 r_{m+1}}{1 - r_{m+1} R_m} \quad (29)$$

$$T_{m+1} = \frac{T_m t_{m+1}}{1 - r_{m+1} R_m} \quad (30)$$

The above iteration of Eqs. (29)-(30) could be repeated until reaching the last interface or the last layer of infinite thickness in a model. The transmittance and reflectance of the entire structure is hence analyzed.

Sometimes, significant simplification of the forward model with minimal parameters is employed, if a quick and coarse evaluation of the ocular surface is enough. For example, in one simplified model, the everted eyelid is modeled as a single layer with different concentration of hemoglobin, collagen, and lipids, etc. core components, and its thickness is modeled as semi-infinite, and after analysis, a 2D distribution of these core components is obtained.

Different polarization states of the polarizer-analyzer pairs reveal different information of the ocular surface and adjacent structures. For example, while a pair of parallel linear polarizers mostly present the surface reflection of tissues; a pair of cross linear polarizers will typically show underlying tissues. Cross linear polarizers could also significantly reduce the glare of adjacent skin or conjunctival tissues. In meibography and scleral imaging, cross linear polarizers filter out light traveling deeper into the tissues, since the polarization state tends to change after multiple scatterings in the underlying tissues, hence part of the scattered light will be able to pass through the analyzer. Precise polarimetric analysis involves Fresnel equations similar to Eq.(9)-(11), which is critical for oblique incidence. The forward model could include the analyses of a plurality of polarizer-analyzer layouts.

In the inverse model, the hyperspectral data is used to estimate the characterization parameters of the ocular surface and adjacent tissues:

$$x \rightarrow p \quad (31)$$

The inverse model could be parametric or non-parametric. If a parametric method of the inverse model is used, the inverse process of the forward model is used to recover the characterization parameters. The parameter estimation based on the inverse function $f^{-1}$ of the forward model in Eq.(8) is usually difficult to obtain analytically due to the nonlinearities in the forward model. However, the parameter estimation could be obtained numerically, if the previous forward mapping function $f$ of different combination of parameters is unique. Numerical parameter estimations are obtained after iterations starting from a guess solution with numerical methods such as Newton-Raphson method, Broyden's method, bisection method, etc. The guess solution is randomly chosen within a preset parameter range based on a priori knowledge of the tissue properties. Usually the Jacobian matrix or other similar derivative-based matrices are used in the iteration process. Sometimes, an inverse model based on least-square minimization, maximum likelihood, independent component analysis, or other parametric methods could be used for parameter estimation of simplified models of the ocular surface and adjacent tissues.

If non-parametric methods are used in the inverse model, the ocular characterization parameters could be estimated with a machine learning method. In the following, a support vector machine based regression method as a non-parametric machine learning method for the inverse model is described.

The input training data points are $\{(x_1, p_1), (x_2, p_2), \ldots, (x_{l-1}, p_{l-1}), (x_l, p_l)\}$, where $x_i \in \mathbb{R}^M$, $p_i \in \mathbb{R}^1$; and the subscript "l" denotes the number of available training data pairs. The training data could be generated with the aforementioned forward model, or collected from experiments. The goal of the inverse model is to find a function g(x) to estimate each scalar component $p_i$ of the target vector p with a maximum deviation of $\varepsilon$:

$$g(x) = \langle w, x \rangle + b \quad (32)$$

Hence given a spectral response vector $x_i$ at a given spatial point, $g(x_i)$ is used to estimate $p_i$. However, the $\varepsilon$-precision might not be a feasible constraint sometimes, and slack variables $\xi_i$ and $\xi_i^*$ could be introduced to relax the error precision $\varepsilon$ to allow some more errors of potential outliers, with a so-called "soft margin", and the constrained optimization problem has the formulation:

$$\text{minimize } \frac{1}{2}\|w\|^2 + C\sum_{i=1}^{l}(\xi_i + \xi_i^*) \qquad (33)$$

$$\text{subject to } \begin{cases} p_i - \langle w, x_i \rangle - b \leq \varepsilon + \xi_i \\ \langle w, x_i \rangle + b - p_i \leq \varepsilon + \xi_i^* \\ \xi_i, \xi_i^* \geq 0 \end{cases}$$

where $\|w\|^2 = \langle w, w \rangle$, and the constant C determines the allowed amount of deviation of the error larger than $\varepsilon$.

The above constrained optimization problem could be simplified by solving a dual problem with Lagrange multipliers. The Lagrangian function is defined as:

$$L = \frac{1}{2}\|w\|^2 + C\sum_{i=1}^{l}(\xi_i + \xi_i^*) - \sum_{i=1}^{l}(\gamma_i \xi_i + \gamma_i^* \xi_i^*) - \sum_{i=1}^{l}\alpha_i(\varepsilon + \xi_i - p_i + \langle w, x_i \rangle + b) - \sum_{i=1}^{l}\alpha_i^*(\varepsilon + \xi_i^* + p_i - \langle w, x_i \rangle - b) \qquad (34)$$

where $\gamma_i$, $\gamma_i^*$, $\alpha_i$, and $\alpha_i^*$ are Lagrange multipliers, which are assistant parameters. From the saddle point condition, the partial derivatives of the Lagrangian function have to vanish, hence $$\frac{\partial L}{\partial b} = \sum_{i=1}^{l}(\alpha_i^* - \alpha_i) = 0 \qquad (35)$$

$$\frac{\partial L}{\partial w} = w - \sum_{i=1}^{l}(\alpha_i - \alpha_i^*)x_i = 0 \qquad (36)$$

$$\frac{\partial L}{\partial \xi_i} = C - \alpha_i - \gamma_i = 0 \qquad (37)$$

$$\frac{\partial L}{\partial \xi_i^*} = C - \alpha_i^* - \gamma_i^* = 0 \qquad (38)$$

Substitute Eq.(36) into Eq.(32), the support vector expansion is obtained as $$g(x) = \sum_{i=1}^{l}(\alpha_i - \alpha_i^*)\langle x_i, x \rangle + b \qquad (39)$$

The dot product $\langle x_i, x \rangle$ in Eq.(39) can be construed to be a measure of similarity. For many applications, including ocular surface evaluation, a nonlinear kernel function $K(x_i, x)$ can be constructed as a generalized measure of similarity, and the nonlinear support vector expansion is $$g(x) = \sum_{i=1}^{l}(\alpha_i - \alpha_i^*)K\langle x_i, x \rangle + b \qquad (40)$$

Common kernel functions include a polynomial kernel such as $K(x_i, x_j) = (x_i \cdot x_j + 1)^p$, a radial basis function kernel or a Gaussian kernel, such as $K(x_i, x_j) = \exp(-\|x_i - x_j\|^2 / 2\sigma^2)$, and a sigmoid kernel, such as $K(x_i, x_j) = \tanh(\kappa x_i \cdot x_j - \delta)$.

The constant offset parameter b could be computed with the Karush-Kuhn-Tucker (KKT) conditions, which states that the products between Lagrange multipliers and the constraints have to vanish, $$\alpha_i(\varepsilon + \xi_i - p_i + \langle w, x_i \rangle + b) = 0 \qquad (41)$$

$$\alpha_i^*(\varepsilon + \xi_i^* + p_i - \langle w, x_i \rangle - b) = 0 \qquad (42)$$

$$(C - \alpha_i)\xi_i = 0 \qquad (43)$$

$$(C - \alpha_i^*)\xi_i^* = 0 \qquad (44)$$

Together with the analysis of the Lagrange multipliers, b could be computed.

In the support vector regression analysis, each parameter of the input characterization vector $p = [p_1, p_2, \ldots, p_j, \ldots, p_{end}]$, where the j-th layer corresponds to a general form of $p_j = [p_{th}, p_{col}, p_{mel}, p_{car}, p_{bil}, p_{myo}, p_{lip}, p_w, p_{bld}, p_o]$, though the characterization parameters for different layers are different. Any scalar $p_i$ is estimated independently with Eq.(40). Repeat the regression process for all the characterization parameters, and the parameter estimation of the ocular surface and adjacent structures could be obtained in the inverse model.

Similar process of the inverse model could be done with other machine learning methods, such as artificial neural networks, k-nearest neighbors regression, etc.

Figure 20:
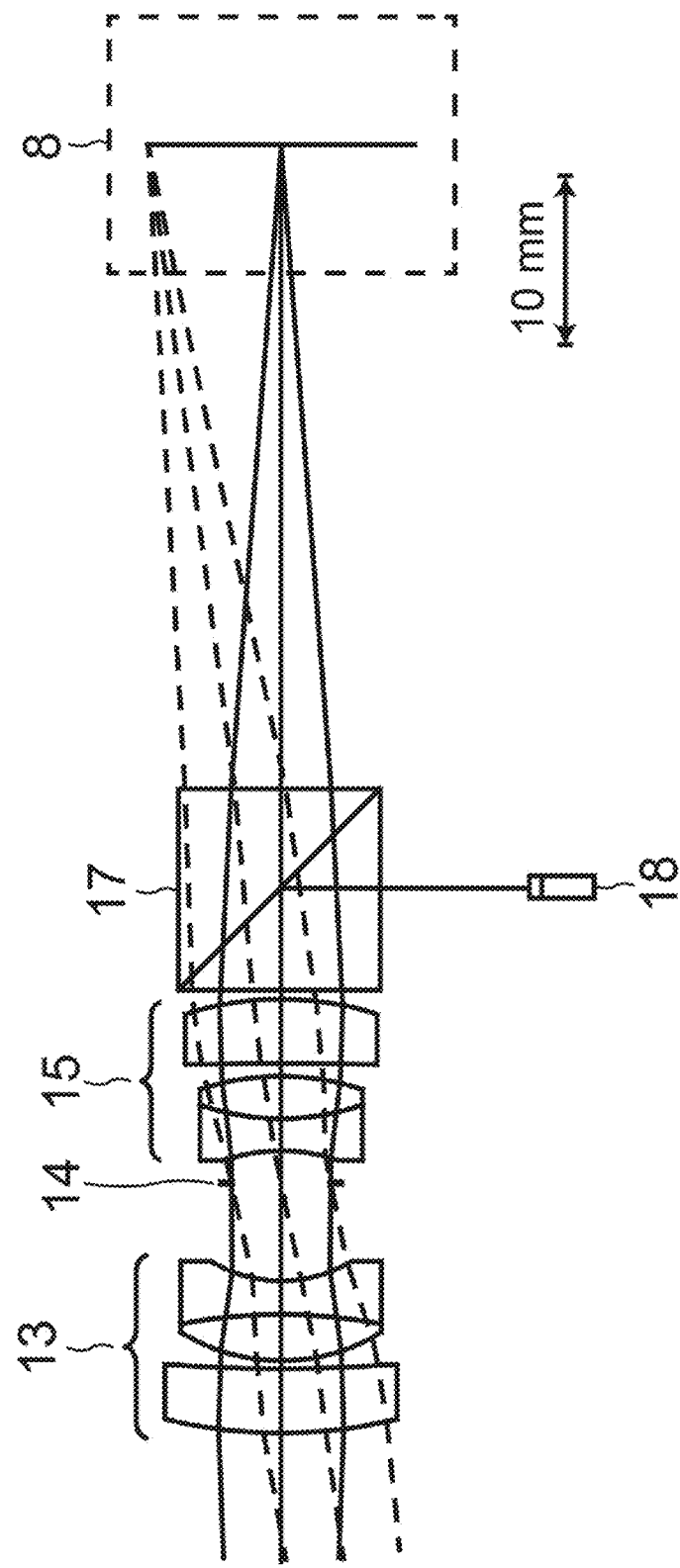
FIG. 20 presents one embodiment of the imaging system and the detection system of a multispectral ocular surface evaluator.

FIG. 20 presents one preferred embodiment of the imaging system and the detection system of a multispectral ocular surface evaluator. It's a double Gauss design optimized for visible and near infrared spectra up to 940 nm, for a sensor with a diagonal length of 16.4 mm. The image F/#=6.5, and magnification=-0.5×. The listed embodiment is illustrative, and by no means the only possible embodiment within the scope of this invention.

The numerical details are listed in Table 1, and the length values are in units of mm.

TABLE 1

| Surface Number | Radius of curvature | Thickness | $n_d$ | $V_d$ | Semi-Aperture |
|---|---|---|---|---|---|
| Object | Infinity | 100 | | | |
| 1 | 29.8092 | 4 | 1.728250 | 28.4102 | 6.51 |
| 2 | 86.1394 | 0.5 | | | 5.98 |
| 3 | 11.6508 | 2.8797 | 1.607381 | 56.6501 | 5.62 |
| 4 | -32.2754 | 2.0920 | 1.603420 | 38.0299 | 5.28 |
| 5 | 8.2170 | 6.0975 | | | 4.08 |
| 6-Stop | Infinity | 2 | | | 3.06 |
| 7 | -10.4825 | 2 | 1.603420 | 38.0299 | 3.37 |
| 8 | 14.9290 | 2.6372 | 1.607381 | 56.6501 | 4.20 |
| 9 | -15.8582 | 0.8 | | | 4.56 |
| 10 | -249.3175 | 4 | 1.670030 | 47.1121 | 4.90 |
| 11 | -19.3742 | 0.5 | | | 5.38 |
| 12 | Infinity | 12.7 | 1.516800 | 64.1673 | 5.46 |
| 13 | Infinity | 40.0296 | | | 5.93 |
| 14-Image | Infinity | | | | 8.20 |

The overall length of this embodiment from the front surface to the image plane is 80.24 mm. From the object side to the image side, Surfaces 1 to 5 is a first Gauss lens group;

Surface 6 is the aperture stop; Surfaces 7 to 11 is a second Gauss lens group; Surfaces 12 to 13 is the preferred beamsplitter for the eye alignment system; Surface 14 is the image plane. The object to front surface distance is 100 mm to have enough space for the illumination system setup. The spacing between Surface 13 and the image plane is 40.03 mm, large enough to place an optional beamsplitter or a scanning mirror of the detection system.

Figure 21:
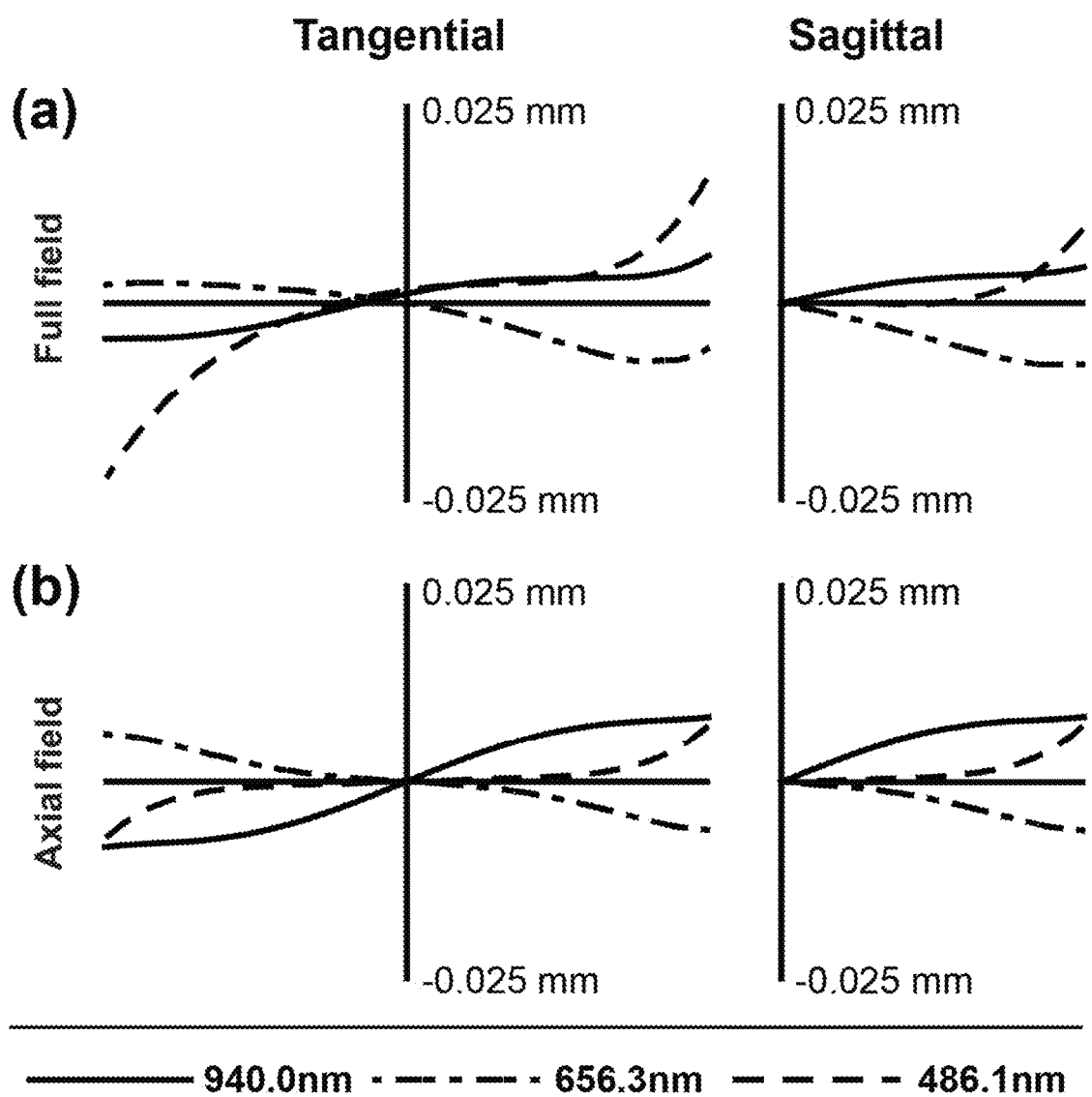
FIG. 21 presents the transverse ray plot of the embodiment in FIG. 20.
Figure 22:
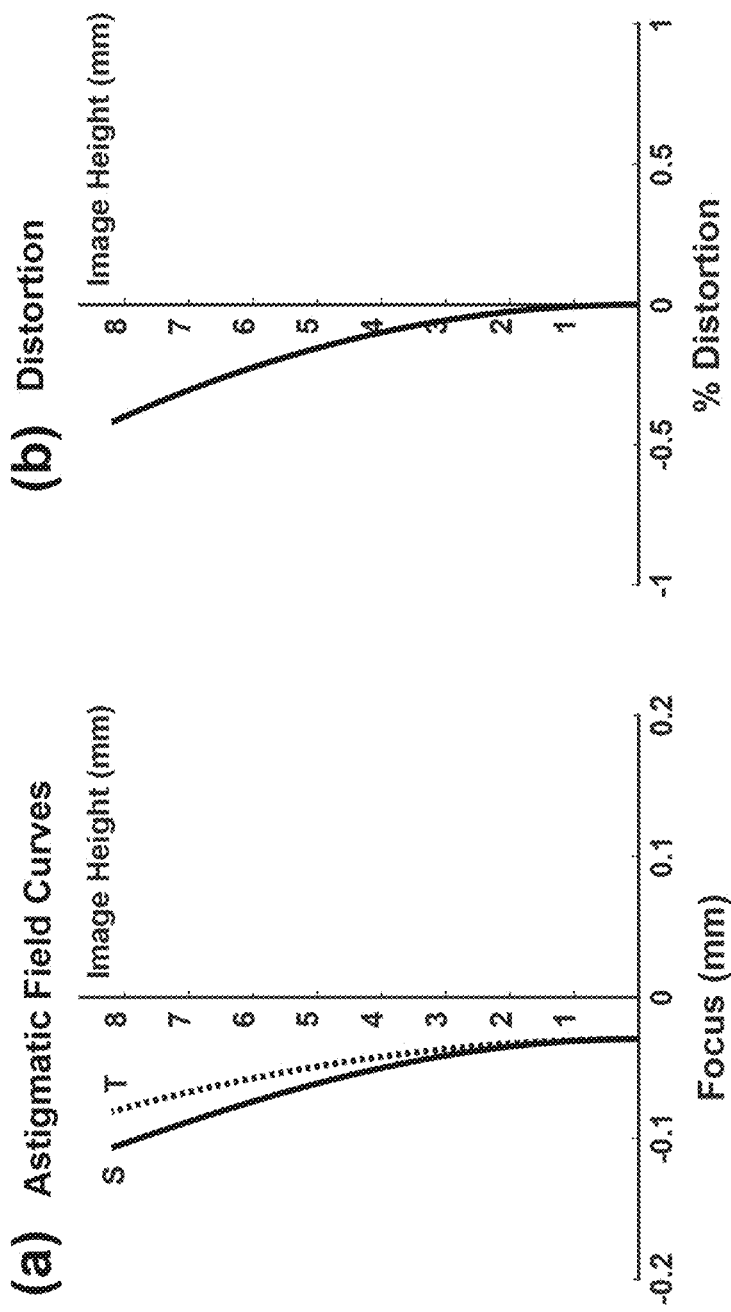
FIG. 22 presents the astigmatic field curves and the distortion of the embodiment in FIG. 20.

FIG. 21 presents the transverse ray plot of the embodiment. FIG. 22 further presents the astigmatic field curves and the distortion.

This invention discloses embodiments and theoretical analyses optimized for a human ocular surface, but those skilled in the art could readily extend the apparatus and method to veterinary ophthalmology to evaluate ocular surfaces of other animals.

All publications, patents and patent applications referred to herein are incorporated by reference in their entirety to the same extent as if each individual publication, patent or patent application was specifically and individually indicated to be incorporated by reference in its entirety in the present application.

The invention has been described in detail with particular reference to certain preferred embodiments thereof, but it will be understood that variations and modifications can be effected within the spirit and scope of the invention.

I claim:

1. A multispectral or hyperspectral ocular surface evaluating device, said device comprising:
    an illumination projector with an aperture in a posterior end of said projector, wherein said illumination projector comprises a broadband illumination source panel and a polarizing structure to illuminate an ocular surface and adjacent structures of an eye and project a pattern on said ocular surface, wherein said broadband illumination source panel covers visible and near infrared spectra;
    an imaging system to form images of said ocular surface and adjacent structures;
    a detection system to record said images with a plurality of spectral channels in visible and near infrared spectra using spectral filters or dispersive optical elements; and
    a computer to display and analyze said images.

2. The apparatus of claim 1, wherein said illumination projector has a shape of rotational symmetry, wherein said illumination projector comprises:
    a broadband illumination source panel with visible and near infrared light-emitting diodes (LEDs);
    a diffusing structure with one or more layers of translucent materials;
    a projection pattern panel; and
    a polarizing structure to control a polarization state distribution of incident light on said ocular surface and adjacent structures.

3. The apparatus of claim 1, wherein said polarizing structure of said illumination projector comprises a member selected from a group consisting of a linear polarizer, a circular polarizer, an elliptical polarizer, a variable polarizer, a sectional polarizing structure with different sections of different polarizing properties, and a combination of a linear polarizer and two high order retarders.

4. The apparatus of claim 1, further comprising:
    a polarization analyzing structure placed in either said imaging system or said detection system.

5. The apparatus of claim 4, wherein said polarization analyzing structure comprises a member selected from a group consisting of a linear polarizer, a circular analyzer, an elliptical analyzer, a rotating polarizer, a variable analyzer, a combination of two high order retarders and a linear polarizer, and a combination of a first Savart plates, a half wave plate, a second Savart plate, and a linear polarizer.

6. The apparatus of claim 1, further comprising:
    an eye alignment system to provide a fixation target for an eye under assessment, wherein said eye alignment system comprises a light source and a beamsplitter, wherein said eye alignment system and said imaging system are aligned coaxially.

7. The apparatus of claim 1, wherein said imaging system comprises a member selected from a group consisting of a fixed focal lens group, a lens group with a magnification changer, and a zoom lens group.

8. The apparatus of claim 1, wherein said detection system is a multispectral detection system, wherein said multispectral detection system comprises a member selected from a group consisting of a detector sensitive to visible and near infrared spectra, a detector with alternating spectral filters, and a combination of detectors and dichroic beamsplitters.

9. The apparatus of claim 1, wherein said detection system is a hyperspectral detection system, wherein said hyperspectral detection system comprises a member selected from a group consisting of a spectrometer system, a snapshot imaging spectrometer system, and a spectral scanning detector.

10. The apparatus of claim 1, wherein a thermal camera is placed paraxially with said imaging system to measure a dynamical thermal change of said ocular surface.

11. The apparatus of claim 1, wherein a retinal polarimeter is added, wherein said retinal polarimeter comprises retinal illumination optics and a compensating lens group.

12. A method of evaluating ocular surface health using a multispectral or hyperspectral ocular surface evaluating device according to claim 1, comprising:
    illuminating an ocular surface and adjacent structures of an eye with polarized light from an illumination projector, covering visible and near infrared spectra;
    forming images of said ocular surface and adjacent structures of said eye with said imaging system;
    recording images formed on said detection system;
    digitally processing said recorded images to obtain spatial and spectral information; and
    analyzing said recorded images to evaluate ocular surface health with said computer.

13. The method of claim 12, wherein said digital processing comprises:
    image preprocessing;
    feature extraction; and
    parameter estimation, wherein characterization parameters of said ocular surface and adjacent structures are estimated.

14. The method of claim 13, wherein said parameter estimation comprises a multi layer model of said ocular surface and adjacent structures, wherein each layer is modeled by said characterization parameters, wherein an inverse model based on a parametric method or a machine learning method is used for said parameter estimation.

15. The method of claim 12, wherein analyzing comprises analyzing reflected images of said illumination projector off said ocular surface to determine a topography of said ocular surface.

16. The method of claim 12, wherein analyzing comprises evaluating a time interval between a last blink and an occurrence of a disrupted area of a pattern of reflected images of said illumination projector off said ocular surface to determine a tear breakup time.

17. The method of claim 12, wherein said analyzing comprises inspecting ocular features with said plurality of spectral channels of said detection system, wherein said ocular features comprises a member selected from a group consisting of tear meniscus height, bases of eyelashes, meibomian gland orifices, and meibomian glands of an everted eyelid.

18. The method of claim 12, wherein said analyzing comprises quantitatively evaluating a bulbar redness and a palpebral redness of the eye based on a conjunctival vascular distribution.

19. The method of claim 12, wherein said analyzing comprises determining lipid layer thickness by polarimetric reflectance values in said plurality of spectral channels of said detection system.

20. The method of claim 12, wherein said analyzing comprises determining corneal birefringence.

\* \* \* \* \*